United States Patent [19]

Krishnamurthy et al.

[11] Patent Number: 4,853,319
[45] Date of Patent: Aug. 1, 1989

[54] PHOTOGRAPHIC SILVER HALIDE ELEMENT AND PROCESS

[75] Inventors: Sundaram Krishnamurthy, Penfield; Brian H. Johnston; Kenneth N. Kilminster, both of Rochester; David C. Vogel, Holcomb, all of N.Y.; Paul R. Buckland, St. Albans, United Kingdom

[73] Assignee: Eastman Kodak Company, Rochester, N.Y.

[21] Appl. No.: 132,531

[22] Filed: Dec. 14, 1987

Related U.S. Application Data

[63] Continuation-in-part of Ser. No. 944,095, Dec. 22, 1986, abandoned.

[51] Int. Cl.$^4$ ................................................ G03C 7/38
[52] U.S. Cl. .................................. 430/387; 430/505; 430/555
[58] Field of Search ..................... 430/387, 555, 505

[56] References Cited

U.S. PATENT DOCUMENTS

| | | | |
|---|---|---|---|
| 3,935,015 | 1/1976 | Arai et al. | 96/74 |
| 4,351,897 | 9/1982 | Aoki et al. | 430/555 |
| 4,413,054 | 11/1983 | Mitsui et al. | 430/555 |
| 4,483,918 | 11/1984 | Sakai et al. | |
| 4,556,630 | 12/1985 | Furutachi et al. | 430/372 |
| 4,585,728 | 4/1986 | Furutachi et al. | 430/372 |
| 4,595,650 | 6/1986 | Furutachi et al. | 430/387 |

FOREIGN PATENT DOCUMENTS

| | | |
|---|---|---|
| 3318759 | 5/1983 | Fed. Rep. of Germany . |
| 60-057839 | 4/1985 | Japan . |

Primary Examiner—Paul R. Michl
Assistant Examiner—Mark R. Buscher
Attorney, Agent, or Firm—Richard E. Knapp

[57] ABSTRACT

Novel pyrazolone photographic couplers contain in the coupling position a coupling-off group represented by the formula:

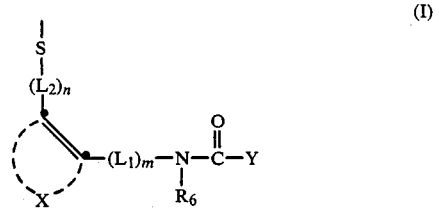

wherein:
$L_1$ and $L_2$ individually are unsubstituted or substituted methylene or ethylene;
m and n individually are 0 or 1;
Y is $R_1$ or $ZR_2$;
$R_1$ is an unsubstituted or substituted aryl or heterocyclic group, or is a secondary or tertiary carbon group represented by

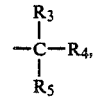

wherein
$R_3$ and $R_4$ are selected from the group consisting of halogen, $R_2$ and $Z_1R_b$; wherein Z is O, S, or $NR_a$; $Z_1$ is O, S, or $NR_c$; and $R_2$ is an unsubstituted or substituted alkyl, aryl, or heterocyclic group. $R_5$, $R_6$, $R_a$, $R_b$ and $R_c$ are as defined in the specification. $R_3$ optionally joins together with at least one of $R_4$ and $R_5$ to form one or two alicyclic or heterocyclic rings, which are optionally further substituted; and
X represents the atoms selected from a group consisting of carbon, oxygen, nitrogen, and sulfur atoms necessary to complete a 5-, 6-, or 7-member unsaturated ring. This ring optionally contains further substituents than those indicated above, including other rings fused to the ring containing X.

These couplers are useful in photographic elements and processes.

13 Claims, No Drawings

PHOTOGRAPHIC SILVER HALIDE ELEMENT AND PROCESS

This is a continuation-in-part of Ser. No. 944,095 of Krishnamurthy et al, filed Dec. 22, 1986, now abandoned, titled "Photographic Silver Halide Element and Process".

This invention relates to novel pyrazolone magenta dye-forming couplers having a particular thio coupling-off group that enables improved image-dye stability.

In color photographic silver halide materials and processes pyrazolone couplers comprising arylthio coupling-off groups have provided magenta dye images having useful properties. Examples of such compounds are described in, for example, U.S. Pat. No. 4,413,054, Japanese published patent application 60/057839 and U.S. Pat. No. 4,351,897. An example of such a pyrazolone coupler described in, for example, U.S. Pat. No. 4,413,054 is designated herein as comparison coupler A and is represented by the formula:

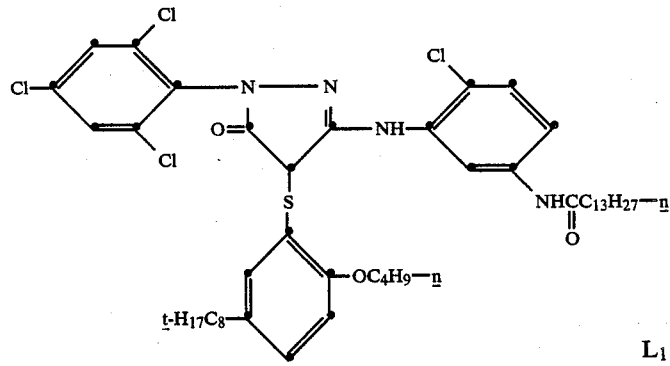

The presence of an alkoxy group in the ortho position on the phenylthio coupling-off group of this compound has provided advantageous properties. However, this coupler has not been entirely satisfactory due to formation of undesired stain in a color photographic silver halide element upon exposure and processing and does not provide desired image-dye density upon rapid machine processing. The coupler A does not achieve full dye density, especially when the exposed color photographic element is machine processed without the presence of Lippman fine grain silver halide being present in the photographic element. It has been desirable to reduce or avoid the need for added Lippman fine grain silver halide without diminishing dye density in the processed color photographic silver halide element. The prior art coupler A does not answer this problem.

It has been desired to provide a color photographic silver halide element and process which is capable of forming a magenta dye image of good dye hue and stability, with high dye yield based on rapid machine processing, with reduction or omission of Lippman fine grain silver halide in the element.

It has been found that this is provided in a color photographic silver halide element by a new 5-pyrazolone photographic coupler containing in the coupling position a coupling-off group represented by the formula:

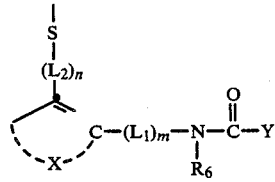

wherein:

$L_1$ and $L_2$ individually are unsubstituted or substituted methylene or ethylene;

m and n individually are 0 or 1;

Y is $R_1$ or $ZR_2$;

$R_1$ is an unsubstituted or substituted aryl or heterocyclic group, or is a secondary or tertiary carbon group represented by

wherein $R_3$ and $R_4$ individually are selected from the group consisting of halogen, $R_2$ and $Z_1R_b$; wherein Z is O, S, or $NR_a$; $Z_1$ is O, S, or $NR_c$; and $R_2$ is an unsubstituted or substituted alkyl, aryl, or heterocyclic group. $R_5$ is hydrogen or as defined for $R_3$ and $R_4$, that is, halogen, an unsubstituted or substituted alkyl, aryl or heterocyclic group or $Z_1R_b$. $R_6$, $R_a$ and $R_c$ are optionally hydrogen or as defined for $R_2$. $R_b$ is an unsubstituted or substituted alkyl, aryl or heterocyclic group, and when $Z_1$ is O then $R_b$ is other than substituted phenyl. $R_3$ optionally joins together with at least one of $R_4$ and $R_5$ to form one or two alicyclic or heterocyclic rings, which are optionally further substituted.

X represents the atoms selected from a group consisting of carbon, oxygen, nitrogen, and sulfur atoms necessary to complete a 5-, 6-, or 7-member unsaturated ring. This ring optionally contains further substituents than those indicated above, including other rings fused to the ring containing X.

The pyrazolone coupler can be a monomeric, oligomeric or polymeric coupler, wherein the coupler moiety can be attached to the polymeric backbone via a substituent on the pyrazolone nucleus, or a substituent of the coupling-off group.

A particularly useful pyrazolone coupler is represented by the formula:

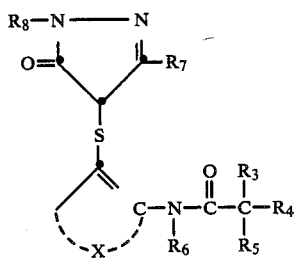

wherein:

$R_6$ and X are as defined;

$R_7$ is an anilino, acylamino, ureido, carbamoyl, alkoxy, aryloxycarbonyl, alkoxycarbonyl, or N-heterocyclic group, preferably such a group that comprises a ballast moiety; and $R_8$ is unsubstituted or substituted aryl, such as substituted phenyl, preferably 2,4,6-trichlorophenyl.

Another particularly useful pyrazolone coupler is represented by the formula:

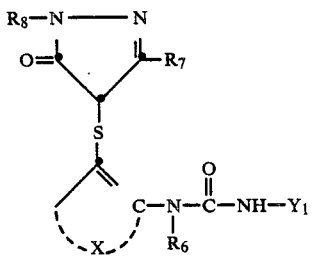

wherein $Y_1$ is an unsubstituted or substituted alkyl, aryl or heterocyclic group;

$R_6$, $R_7$, and $R_8$ are as defined. $R_7$ in this particularly useful coupler is typically —NH—$Y_3$ wherein $Y_3$ is unsubstituted or substituted aryl, arylcarbonyl or arylaminocarbonyl. $R_8$ is typically 2,4,6-trichlorophenyl. An illustrative $R_7$ group is

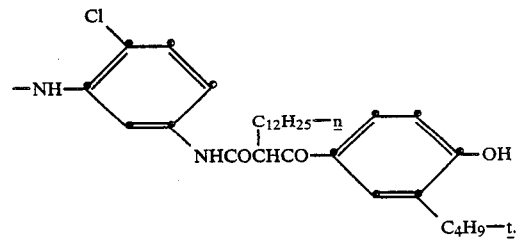

The term "coupler" herein refers to the entire compound, including the coupler moiety and the coupling-off group. The term "coupler moiety (COUP)" refers to that portion of the compound other than the coupling-off group.

The coupler moiety (COUP) can be any pyrazolone coupler moiety known or used in the photographic art to form a color reaction product particularly a magenta dye, with oxidized color developing agent. Examples of useful pyrazolone coupler moieties are described in, for example, U.S. Pat. Nos. 4,413,054; 4,443,536; 4,522,915; 4,336,325; 4,199,361; 4,351,897; and 4,385,111; Japanese Published Patent Application Nos. 60/170854; 60/194452; and 60/194451; U.S. Pat. Nos. 4,407,936; 3,419,391; and 3,311,476; U.K. Pat. No. 1,357,372; U.S. Pat. Nos. 2,600,788; 2,908,573; 3,062,653; 3,519,429; 3,152,896; 2,311,082; 2,343,703; and 2,369,489, the disclosures of which are incorporated herein by reference. The coupling-off group, if any, on the pyrazolone coupler moiety described in these patents or patent applications can be replaced by a coupling-off group according to the invention (structure I). The pyrazolone coupler according to the invention can be in a photographic element in combination with pyrazolone couplers known or used in the photographic art, such as in combination with at least one of the pyrazolone couplers described in these patents or published patent applications.

An example of a useful COUP is represented by the formula:

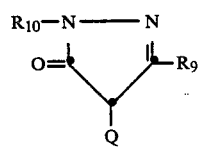

wherein

Q represents a coupling-off group according to the invention and wherein:

$R_9$ is an anilino, acylamino, ureido, carbamoyl, alkoxy, aryloxycarbonyl, alkoxycarbonyl, or N-heterocyclic group; and $R_{10}$ is unsubstituted or substituted aryl, such as phenyl containing at least one substituent selected from halogen atoms, alkyl, alkoxy, alkoxycarbonyl, acylamino, sulfamido, sulfonamido and cyano groups. Carbon and nitrogen atoms of these substituents are unsubstituted or optionally substituted with groups that do not adversely affect the coupler.

$R_9$ is typically anilino, such as anilino represented by the formula:

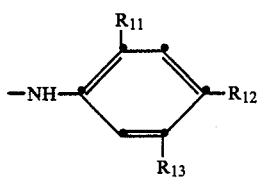

wherein:

$R_{11}$ is alkoxy, such as alkoxy containing 1 to 30 carbon atoms, aryloxy or halogen, typically chlorine;

$R_{12}$ and $R_{13}$ are individually hydrogen; halogen, such as chlorine, bromine or fluorine; alkyl, such as alkyl containing 1 to 30 carbon atoms; alkoxy, such as alkoxy containing 1 to 30 carbon atoms; acylamino; sulfonaido; sulfamoyl; sulfamido; carbamoyl; diacylamino; aryloxycarbonyl; alkoxycarbonyl; alkoxysulfonyl; aryloxysulfonyl; alkanesulfonyl; arenesulfonyl; alkylthio; arylthio; alkoxycarbonylamino; alkylureido; acyl; nitro; and carboxy. $R_{12}$ and $R_{13}$ individually can, for instance, be hydrogen or a ballast group.

$R_{10}$ is typically substituted phenyl; such as phenyl substituted with halogen, for example chlorine, bromine and fluorine; with alkyl, such as alkyl containing 1 to 22 carbon atoms, for example methyl, ethyl, propyl, t-butyl, and tetradecyl; with alkoxy, such as a alkoxy containing 1 to 22 carbon atoms, for example, methoxy, ethoxy and dodecyloxy; with alkoxycarbonyl, such as alkoxycarbonyl containing 1 to 23 carbon atoms, for example, methoxycarbonyl, ethoxycarbonyl, and tetradecyloxycarbonyl; with acylamino, such as α-[3-pentadecylphenoxy]butyramido; and/or with a cyano group. $R_{10}$ is preferably a 2,4,6-trichlorophenyl group.

Examples of $R_{12}$ and $R_{13}$ include hydrogen; halogen, such as chlorine, bromine or fluorine; alkyl, including straight or branched chain alkyl, such as alkyl containing 1 to 30 carbon atoms, for example methyl, trifluoromethyl, ethyl, t-butyl, and tetradecyl; alkoxy, such as alkoxy containing 1 to 30 carbon atoms, for example methoxy, ethoxy, 2-ethylhexyloxy and tetradecyloxy; acylamino, such as acetamido, benzamido, butyramido, tetradecanamido, α-(2,4-di-t-pentylphenoxy)acetamido, α-(2,4-di-t-pentylphenoxy)butyramido, α-(3-pentadecylphenoxy)hexanamido, α-(4-hydroxy-3-t-butylphenoxy)tetradecanamido, 2-oxo-pyrrolidin-1-yl, 2-oxo-5-tetradecyl-pyrrolin-1-yl, N-methyl-tetradecanamido, and t-butylcarbonamido; sulfonamido, such as methanesulfonamido, benzenesulfonamido, p-toluenesulfonamido, p-dodecylbenzenesulfonamido, N-methyltetradecylsulfonamido, and hexadecanesulfonamido; sulfamoyl, such as N-methylsulfamoyl, N-hexadecylsulfamoyl, N,N-dimethylsulfamoyl; N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; sulfamido, such as N-methylsulfamido and N-octadecylsulfamido; carbamoyl, such as N-methylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; diacylamino, such as N-succinimido, N-phthalimido, 2,5-dioxo-1-oxazolidinyl, 3-dodecyl-2,5-dioxo-1-imidazolyl, and N-acetyl-N-dodecylamino; aryloxycarbonyl, such as phenoxycarbonyl and p-dodecyloxyphenoxy carbonyl; alkoxycarbonyl, such as alkoxycarbonyl containing 2 to 30 carbon atoms, for example methoxycarbonyl, tetradecyloxycarbonyl, ethoxycarbonyl, benzyloxycarbonyl, and dodecyloxycarbonyl; alkoxysulfonyl, such as alkoxysulfonyl containing 1 to 30 carbon atoms, for example methoxysulfonyl, octyloxysulfonyl, tetradecyloxysulfonyl, and 2-ethylhexyloxysulfonyl; aryloxysulfonyl, such as phenoxysulfonyl, 2,4-di-t-pentylphenoxysulfonyl. Alkanesulfonyl, such as alkanesulfonyl containing 1 to 30 carbon atoms, for example methanesulfonyl, octanesulfonyl, 2-ethylhexanesulfonyl, and hexadecanesulfonyl; arenesulfonyl, such as benzenesulfonyl, 4-nonylbenzenesulfonyl, and p-toluenesulfonyl; alkylthio, such as alkylthio containing 1 to 22 carbon atoms, for example ethylthio, octylthio, benzylthio, tetradecylthio, and 2-(2,4-di-t-pentylphenoxy)ethylthio; arylthio, such as phenylthio and p-tolylthio; alkoxycarbonylamino, such as ethoxycarbonylamino, benzyloxycarbonylamino, and hexadecyloxycarbonylamino; alkylureido, such as N-methylureido, N,N-dimethylureido, N-methyl-N-dodecylureido, N-hexadecylureido, N,N-dioctadecylureido, and N,N-dioctyl-N'-ethyl-ureido; acyl, such as acetyl, benzoyl, octadecanoyl, p-dodecanamidobenzoyl, and cyclohexanecarbonyl; nitro; cyano and carboxy (—COOH).

Examples of $R_{11}$ as alkoxy include methoxy, ethoxy, propoxy, butoxy, 2-methoxyethoxy, sec-butoxy, hexyloxy, 2-ethylhexyloxy, 2-(2,4-di-t-pentylphenoxy)ethoxy, and 2-dodecyloxyethoxy.

Examples of $R_{11}$ as aryloxy include phenoxy, α- or β-naphthyloxy, and 4-tolyloxy.

Illustrative couplers include:

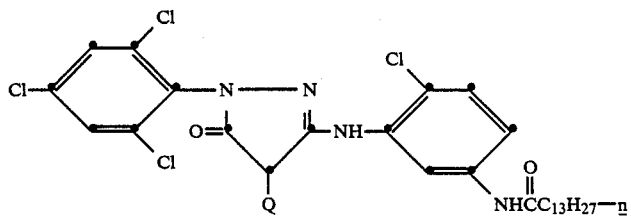

-continued
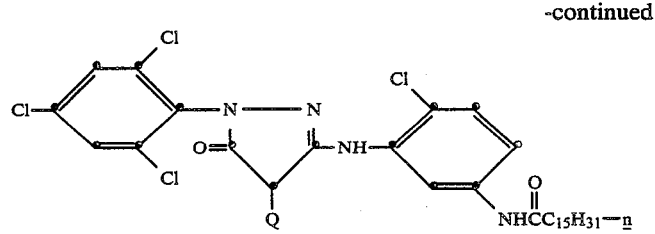
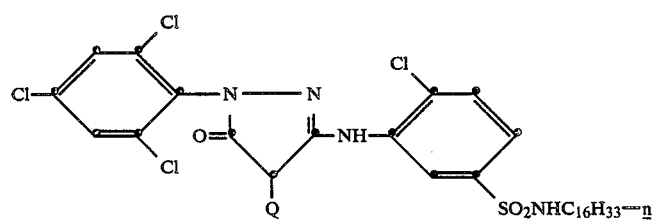
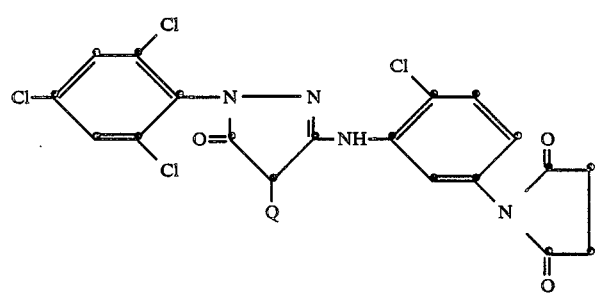
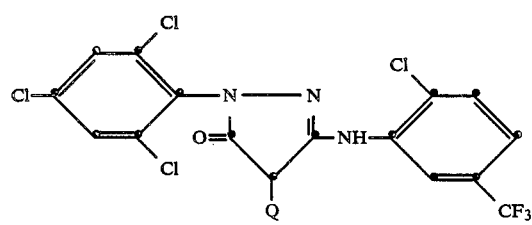
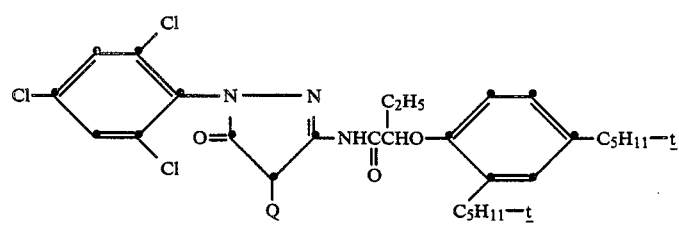
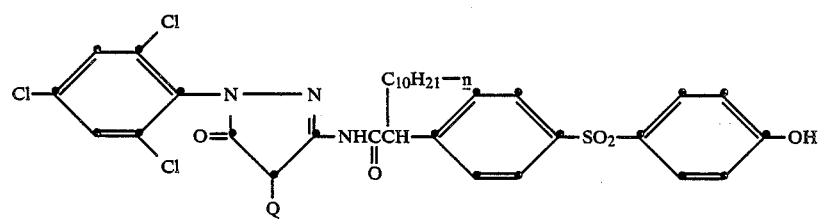
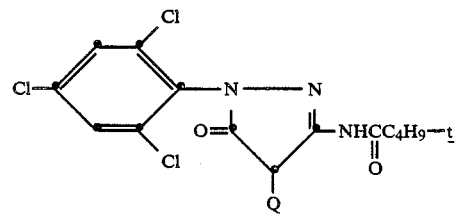

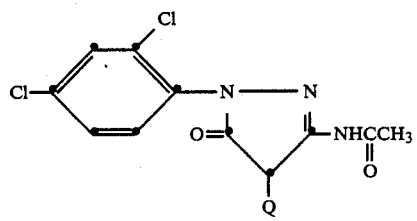
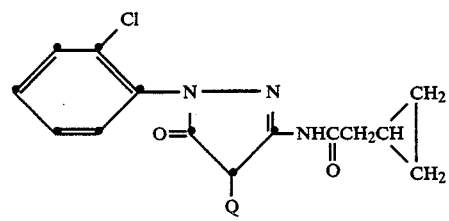
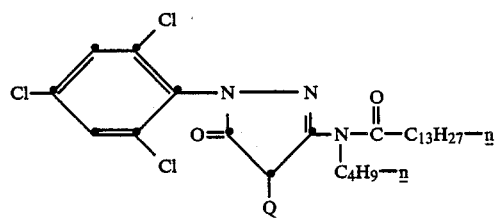
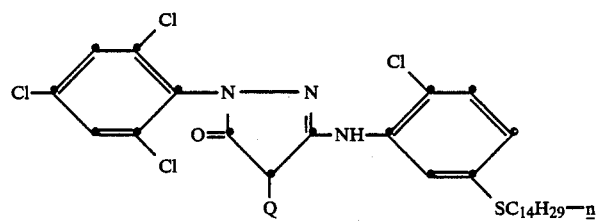
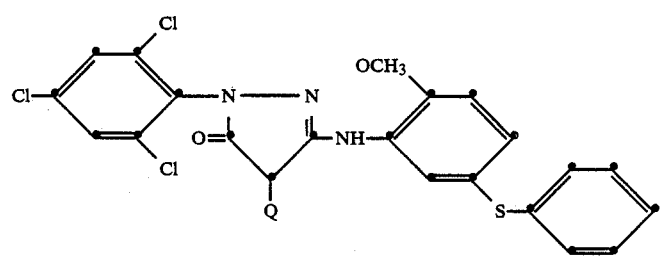
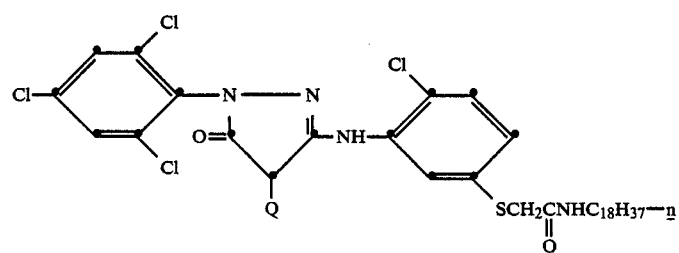
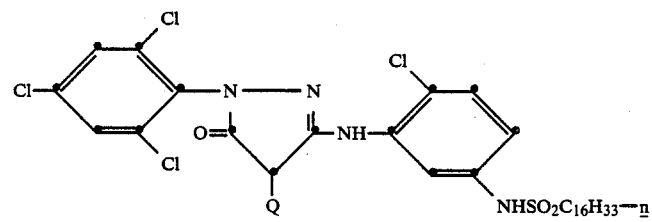

-continued
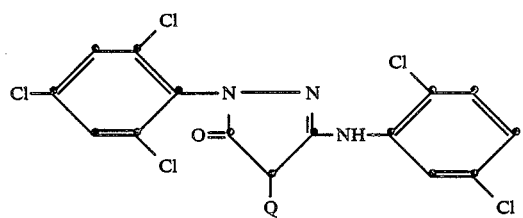
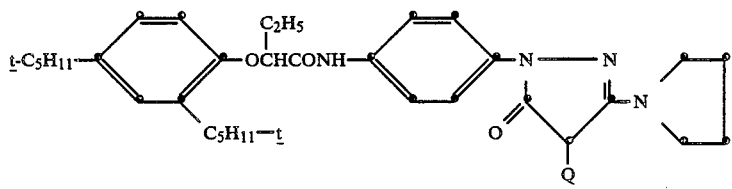
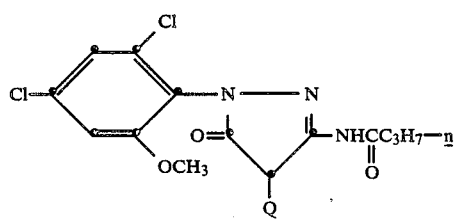
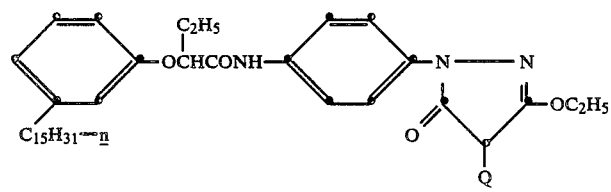
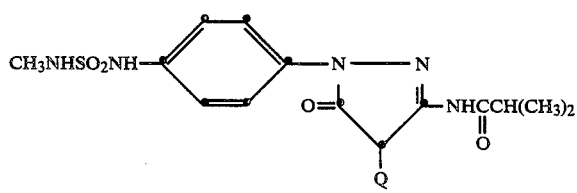
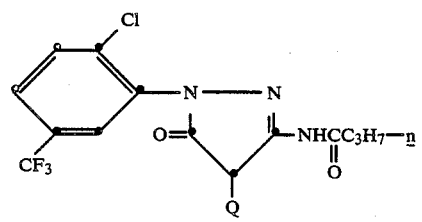
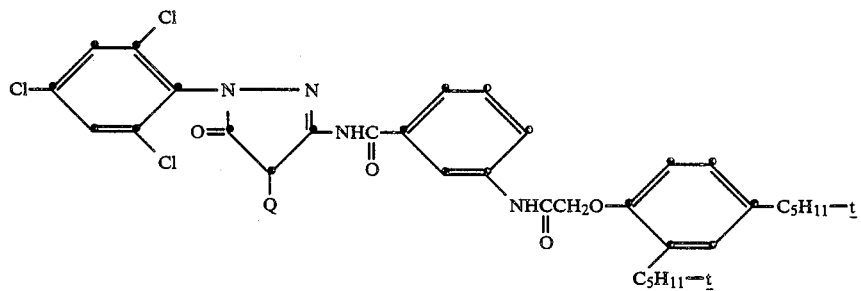

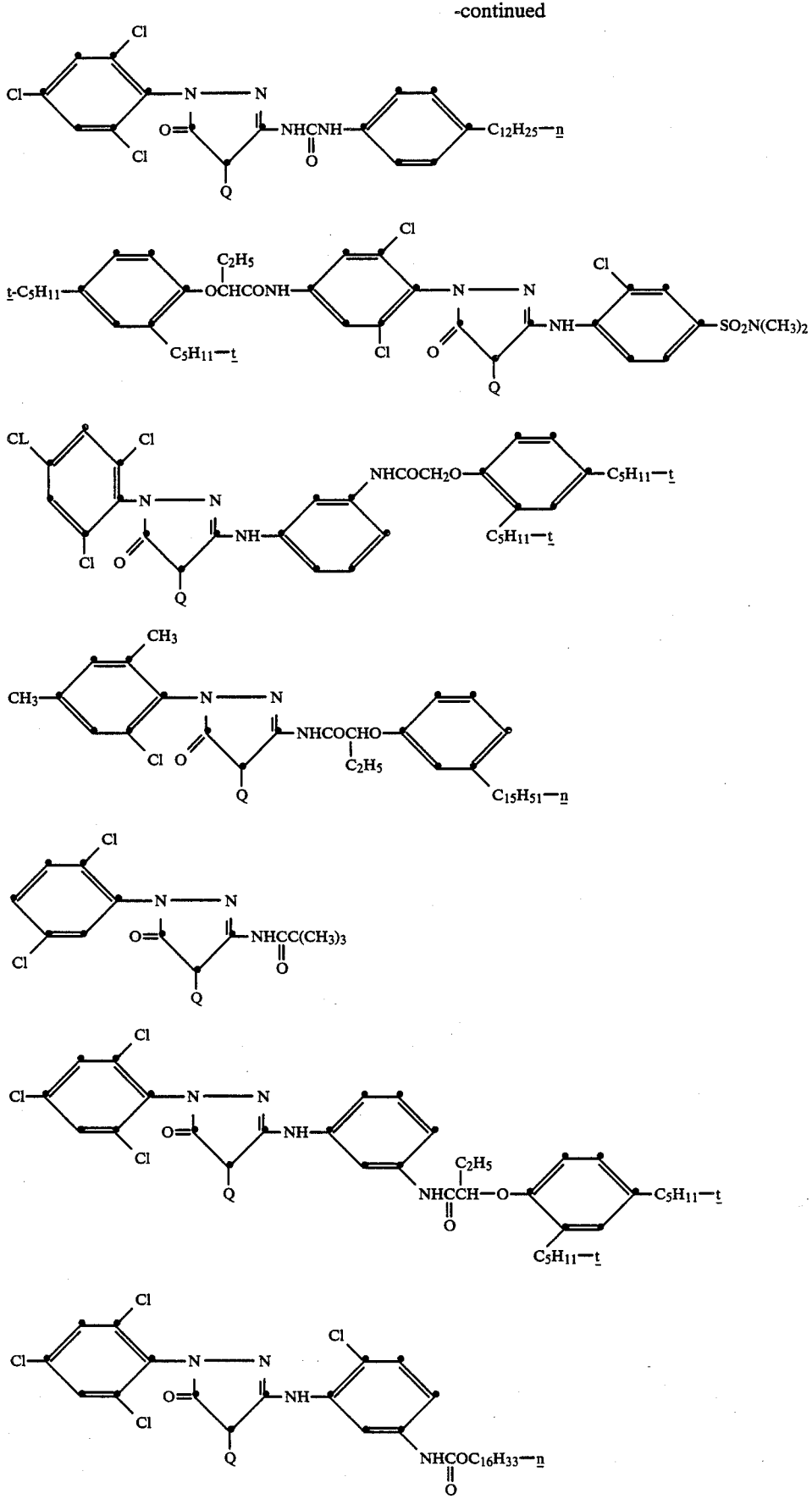

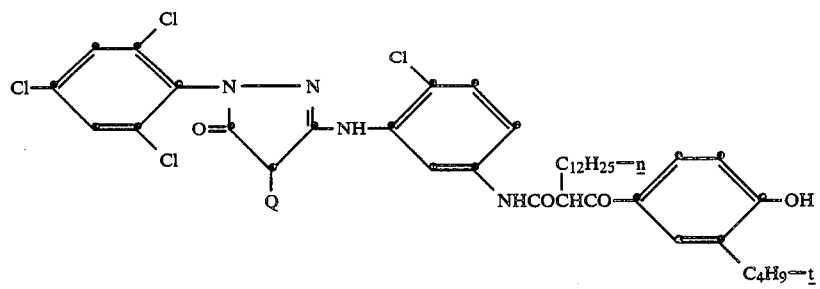

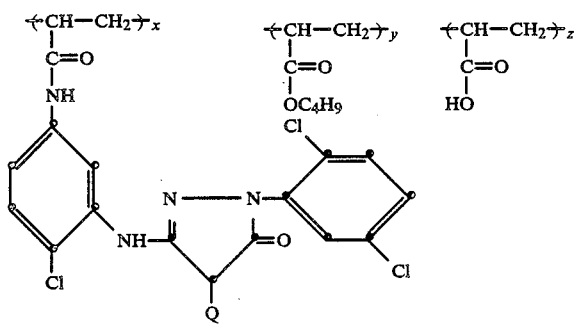

wherein x is 1, y is 2 to 5, and z is 0.1 to 0.5.

Q herein represents a coupling-off group according to the invention.

X in structure I represents the atoms selected from the group consisting of carbon, oxygen, nitrogen and sulfur atoms to complete a 5-, 6- or 7-member unsaturated ring such as an aromatic ring. The ring is, for example, a phenyl, naphthyl, pyridyl, or quinolyl ring. The ring need not contain substituents other than the —(L$_2$)$_n$—S—COUP and

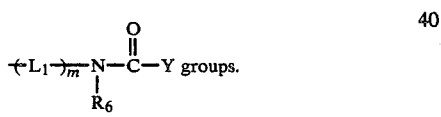

The ring can be optionally further substituted with groups that do not adversely affect the desired properties of the coupler. Substituents that have been used or knownon arylthio coupling-off groups on pyrazolone couplers can be used on the unsaturated ring completed by X. Optional substituents on this ring include at least one of the following: halogen, such as chlorine, fluorine and bromine; acylamino, sulfonamido, alkylthio, hydroxyl, alkyl, alkoxy, aryl, arylthio, and aryloxy. Examples of these substituents are acylamino containing 1 to 30 carbon atoms, such as acetamido, butyramido, tetradecanamido; sulfonamido containing 1 to 30 carbon atoms, such as methanesulfonamido, benzenesulfonamido, p-toluenesulfonamido; alkylthio containing 1 to 22 carbon atoms, such as methylthio, ethylthio, t-butylthio, octadecylthio; alkyl containing 1 to 22 carbon atoms, such as methyl, ethyl, propyl, t-butyl, tetradecyl; alkoxy containing 1 to 22 carbon atoms, such as methoxy, ethoxy, octyloxy, tetradecyloxy; aryl, such as phenyl and tolyl; arylthio, such as phenylthio; and aryloxy, such as phenoxy.

Illustrative coupling-off groups (Q) are as follows:

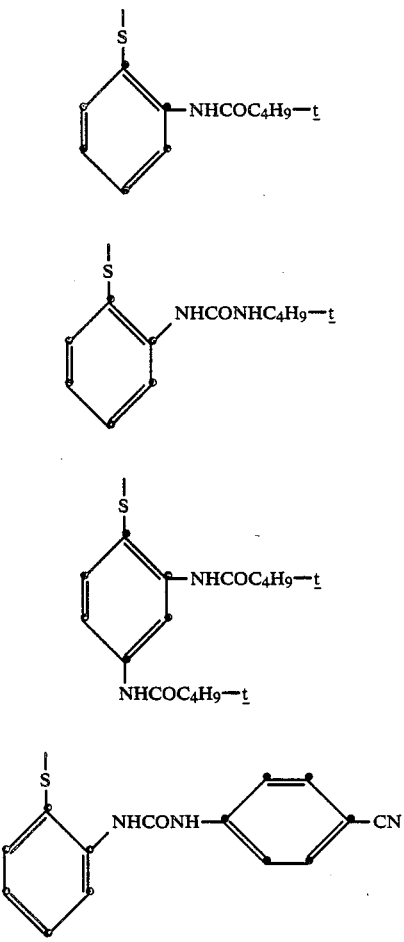

-continued
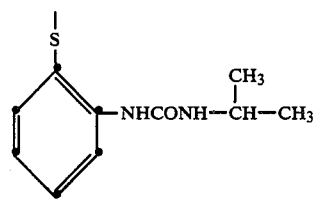
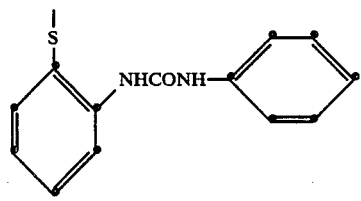
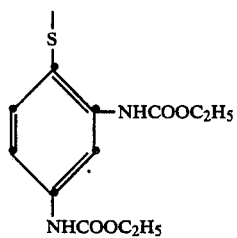
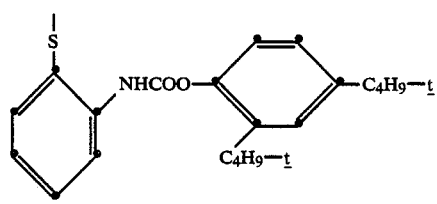
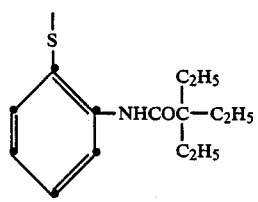
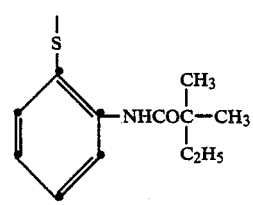
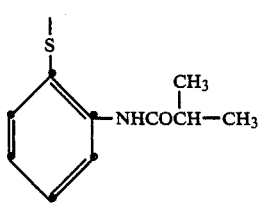
-continued
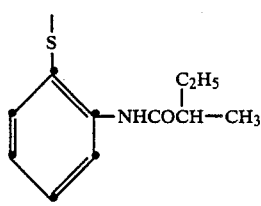
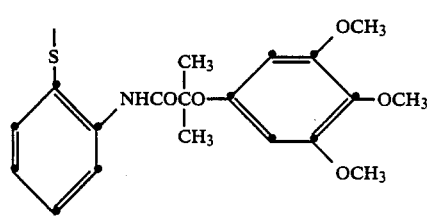
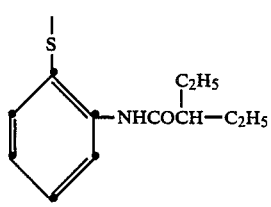
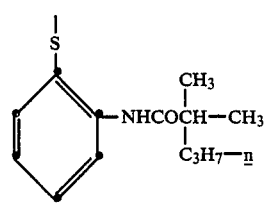
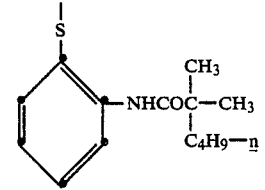
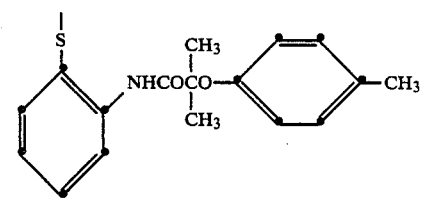
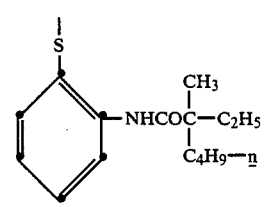

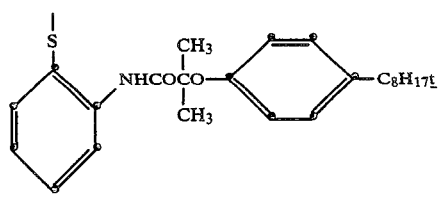
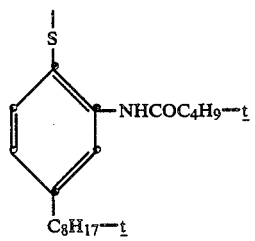
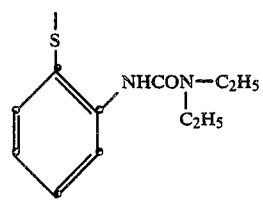
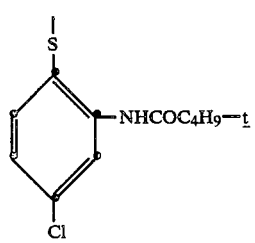
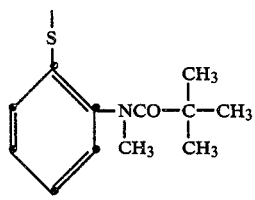
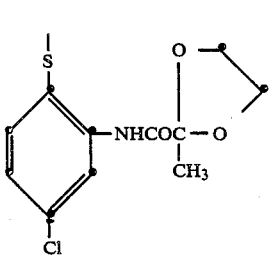
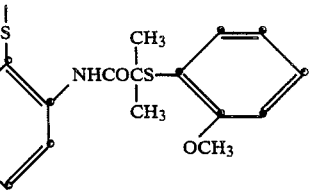
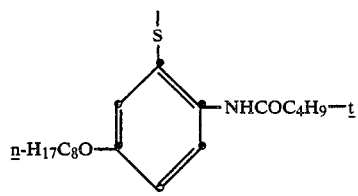
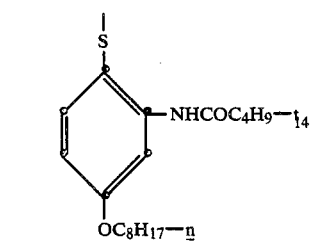
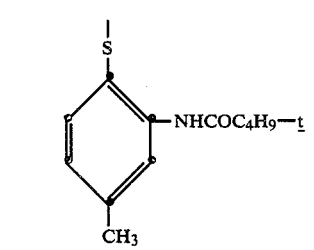
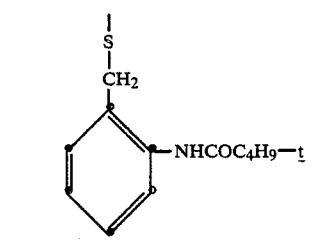
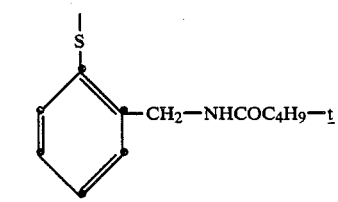
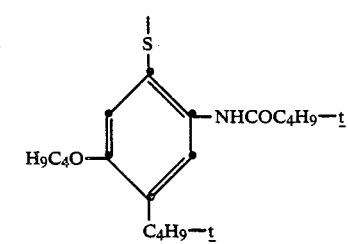

-continued
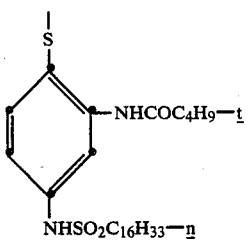
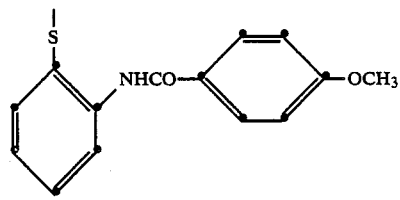
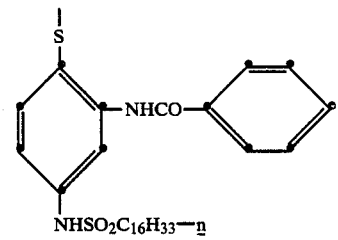
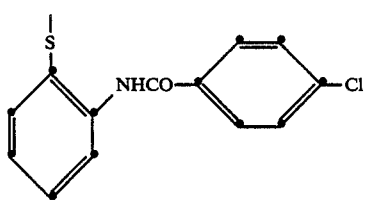
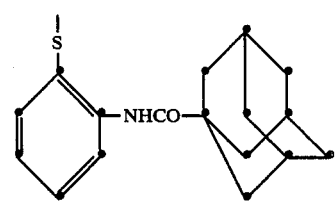
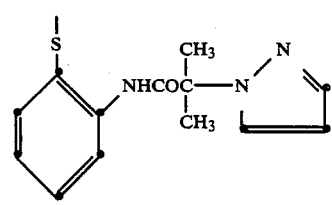
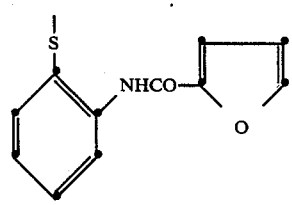
-continued
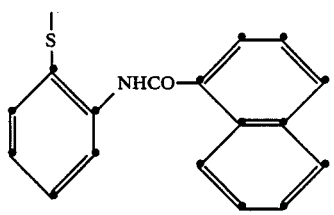
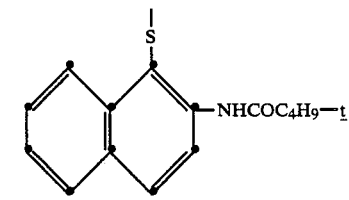
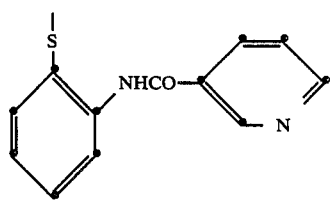
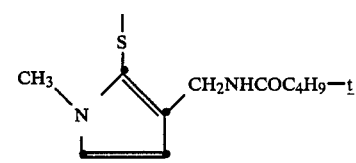
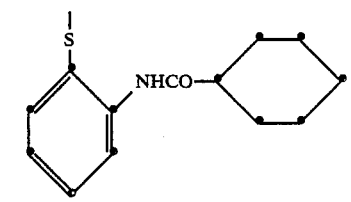
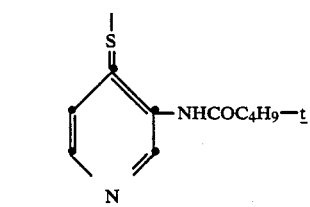
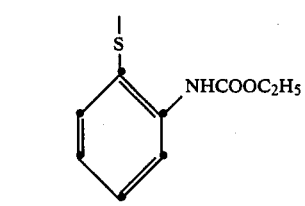

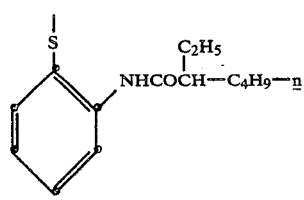

The pyrazolone coupler preferably comprise a ballast group. The ballast group can be any ballast known in the photographic art. The ballast is typically one that does not adversely affect reactivity, stability and other desired properties of the coupler of the invention and does not adversely affect the stability, hue and other desired properties of the dye formed from the coupler. Illustrative useful ballast groups are described in the following examples.

Couplers of this invention can be prepared by reacting the parent 4-equivalent coupler containing no coupling-off group with the disulfide of the coupling-off group according to the invention. This is a simple method and does not involve multiple complicated synthesis steps. The reaction is typically carried out in a solvent, such as dimethylformamide or pyridine.

The couplers according to the invention can be prepared from inexpensive ortho-aminothiophenol compounds by the following illustrative synthetic scheme, where COUP represents the coupler moiety having the coupling-off group attached at its coupling position:

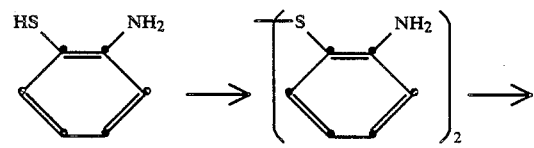

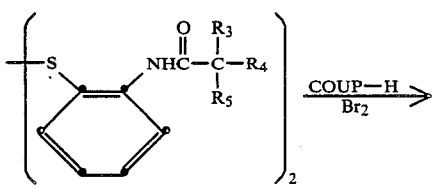

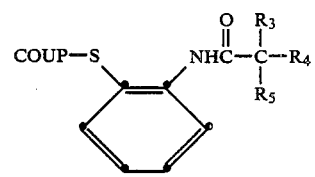

wherein COUP is the coupler moiety and $R_3$, $R_4$ and $R_5$ are as defined.

The following examples illustrate the preparation of couplers of this invention.

SYNTHESIS EXAMPLE A

Preparation of Compound 2:

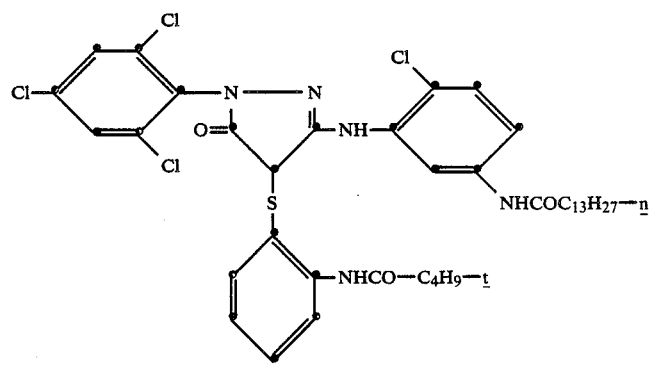

To a solution of 15.3 g (24.9 mmol) Coupler No. M-1 of the formula:

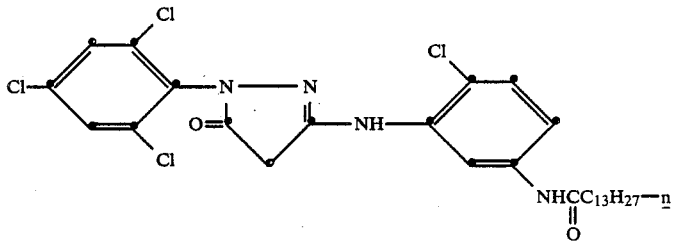

(illustrated in, for example, U.S. Pat. No. 3,935,015) and 5.3 g (12.7 mmol) o-pivalamidophenyl disulfide in 88 mL dimethylformamide was added with stirring 2.1 g (13.1 mmol) bromine in 18 mL dimethylformamide and the mixture was heated 2 hours on a steambath. After standing overnight, the mixture was poured into cold water and the resulting precipitate was collected and washed with water. The crude product was purified, for example, recrystallized from acetonitrile, then from toluene using decolorising carbon, and finally washed with hexane to obtain upon vacuum drying 6.4 g Compound 2 as a colorless solid, m.p. 129°–133° C. Identity of the product was confirmed by its nmr spectrum and elemental analysis.

Elemental analysis (% found vs. % calculated): C=58.2 vs. 58.5; H=5.9 vs. 6.0; N=8.4 vs. 8.5; Cl=17.4 vs. 17.3; S=3.8 vs. 3.9.

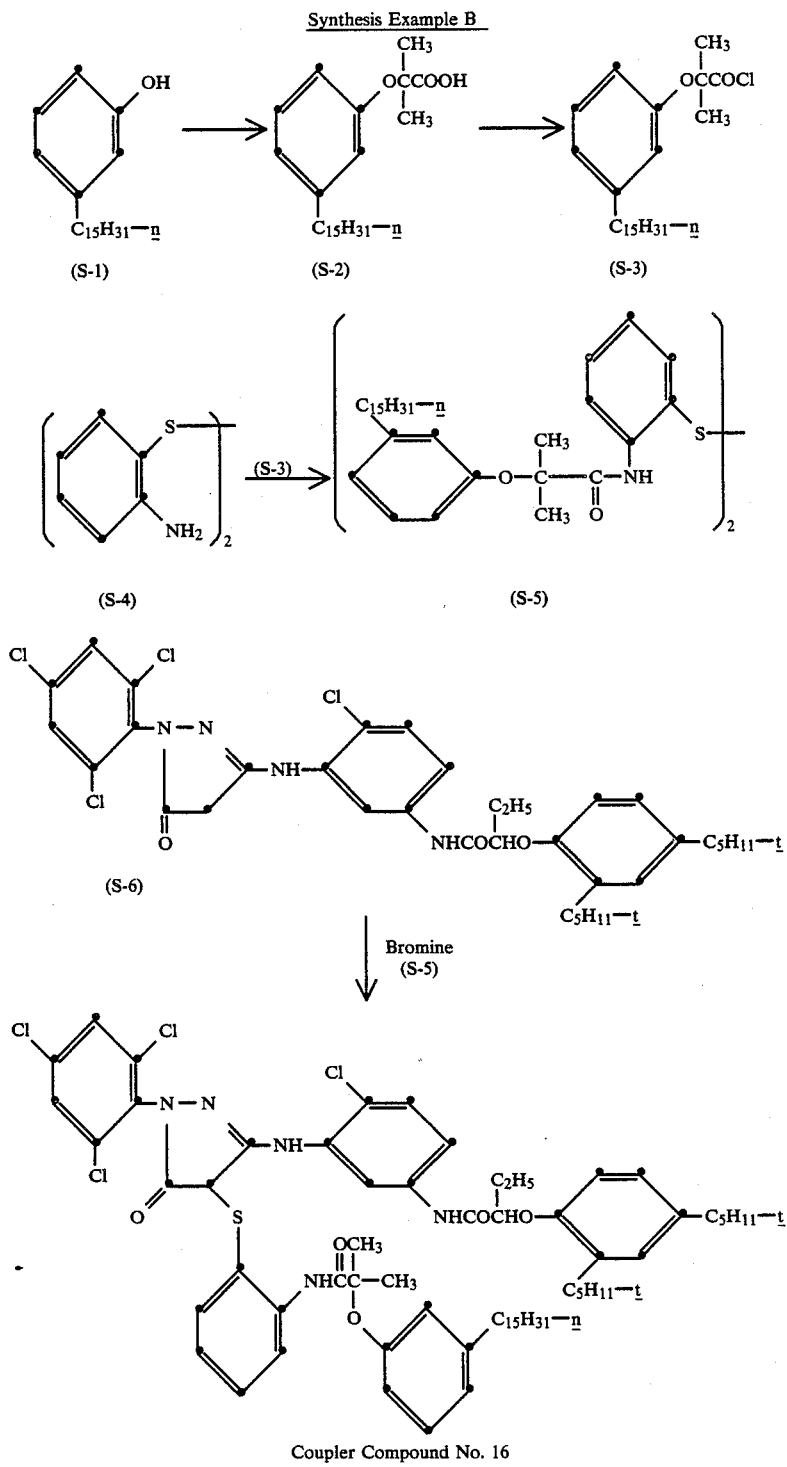

Coupler Compound No. 16

SYNTHESIS EXAMPLE B

Preparation of Compound 16:

To a solution of 30.4 g (0.1 mol) 3-pentadecylphenol (S-1) and 20 g (0.5 mol) sodium hydroxide in 250 mL acetone was added dropwise with stirring at 60° 15.6 g (0.13 mol) chloroform. After 2 hours heat was removed and the mixture allowed to cool overnight. Treatment with 10% hydrochloric acid, extraction of an ethyl acetate solution with saturated sodium carbonate solution, reacidification to pH 2, ether extraction, drying, and concentration yielded 18.3 g acid (S-2). Then 12.6 g (32.3 mmol) S-2 was treated with 20 mL (180 mmol) thionyl chloride, the mixture heated 5 hours at 70° and concentrated to yield 13.2 g acid chloride (S-3). A solution of 12.8 g S-3 in 60 mL tetrahydrofuran was added dropwise to a solution of 2-aminophenyl disulfide (S-4) in 100 mL tetrahydrofuran and stirring continued 30 minutes. The mixture was poured into water, extracted with diethyl ether, the extracts dried, concentrated, and purified by silica gel chromatography to yield 7.3 g ballasted disulfide (S-5).

Next, a solution of 1.2 g (7.7 mmol) bromine in 20 mL dimethylformamide was added dropwise to a solution of 7.5 g (10.6 mmol) magenta coupler (S-6) and 6.0 g (5.9 mmol) disulfide (S-5) in 60 mL dimethylformamide under an argon atmosphere and stirred overnight at 95°. The mixture was poured into ice-water and the resulting precipitate collected as 13.7 g yellow solid. Of this 5.0 g was purified by silica gel chromatography to yield 1.6 g coupler Compound 16 as a brown glassy solid, m.p. 86°–90°. Purity and identity of the product was confirmed by liquid chromatography and an nmr spectrum.

The following compounds were prepared by this general method.

TABLE I

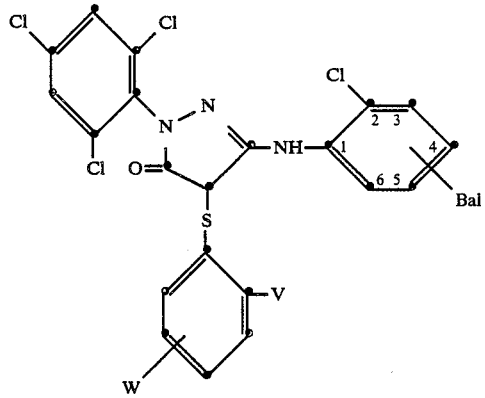

| Cmpd. | W | V | Ball.** | M.p. °C. |
|---|---|---|---|---|
| A* | 5'-C$_8$H$_{17}$—t | —OC$_4$H$_9$—n | B-1 | 165–167 |
| B* | | (Coupling-off group is hydrogen) | B-8 | 179–180 |
| C* | H | —NHCOC$_{11}$H$_{23}$—n | B-1 | 90–115 |
| D* | H | —NHCOC$_7$H$_{15}$—n | B-1 | 115–129 |
| E* | H | —NHCOC$_{11}$H$_{23}$—n | B-2 | 120–124 |
| F* | H | —NHCOC$_{11}$H$_{23}$—n | B-4 | 105–107 |
| G* | H | —NHCOC$_{11}$H$_{23}$—n | B-3 | 135–137 |
| H* | | (Coupling-off group is hydrogen) | B-4 | n/a |
| 1 | H | —NHCOC$_4$H$_9$—t | B-5 | n/a |
| 2 | H | —NHCOC$_4$H$_9$—t | B-1 | 129–133 |
| 3 | H | —NHCOC$_4$H$_9$—t | B-8 | n/a |
| 4 | H | —NHCOC$_4$H$_9$—t | B-2 | n/a |
| 5 | H | —NHCOC$_4$H$_9$—t | B-4 | n/a |
| 6 | H | —NHCOC$_4$H$_9$—t | B-3 | 147–149 |
| 7 | 4'-NHCOC$_4$H$_9$—t | —NHCOC$_4$H$_9$—t | B-2 | 190–193 |
| 8 | 4'-NHCOC$_4$H$_9$—t | —NHCOC$_4$H$_9$—t | B-4 | 143–153 |
| 9 | 4'-NHCOC$_4$H$_9$—t | —NHCOC$_4$H$_9$—t | B-5 | 170–180(dec) |
| 10 | 4'-NHCOC$_4$H$_9$—t | —NHCOC$_4$H$_9$—t | B-1 | 173–174 |
| 11 | H | —NHCOC(Me,Et)Bu—n | B-5 | 115–121(dec) |
| 12 | H | —NHCOC(Me,Me)Bu—n | B-5 | 184–187 |
| 13 | H | —NHCOC(Me,Me)OPh—3-C$_{15}$H$_{31}$—n | B-1 | 69–73 |
| 14 | H | —NHCOC—1-Adamantyl | B-5 | 145–154(dec) |
| 15 I* | H | —NHCOC(Me,Me)OPh—3,4,5-(OMe)$_3$ | B-5 | n/a |
| 16 J* | H | —NHCOC(Me,Me)OPh—3-C$_{15}$H$_{31}$—n | B-5 | 86–90 |
| 17 K* | H | —NHCOC(Me,Me)OPh—3-C$_{15}$H$_{31}$—n | B-6 | 66–70 |
| 18 L* | H | —NHCOC(Me,Me)OPh—4-OC$_8$H$_{17}$ | B-5 | 96–100 |
| 19 M* | H | —NHCOC(Me,Me)OPh—4-Me | B-5 | 114–120 |
| 20 N* | H | —NHCOC(Me,Me)OPh—4-C$_8$H$_{17}$—t | B-5 | 115–119 |
| 21 | H | —NHCOC(Me,Me)SPh—2-OMe | B-5 | 100–105 |
| 22 | H | —NHCOCH(Et)Bu—n | B-3 | 92–94 |
| 23 | H | —NHCOCH(Et)Bu—n | B-2 | 144–147 |
| 24 | H | —NHCOCH(Et)Bu—n | B-4 | n/a |
| 25 | H | —NHCOC$_3$H$_7$—i | B-1 | 110–125 |
| 26 | H | —NHCO—3-Pyridyl | B-1 | n/a |
| 27 | H | —NHCO—1-Naphthyl | B-8 | n/a |
| 28 | H | —NHCOPh—3,4,5-(OMe)$_3$ | B-5 | 135–140 |
| 29 | H | —NHCOPh | B-8 | n/a |
| 30 | H | —NHCOPh—4-Cl | B-8 | n/a |
| 31 | H | —NHCOPh—4-Br | B-8 | n/a |
| 32 | H | —NHCOPh—4-OMe | B-1 | n/a |
| 33 | H | —NHCOPh—4-Cl | B-1 | n/a |
| 34 | H | —NHCOPh | B-1 | n/a |
| 35 | H | —NHCOC(Me,Me)—1-Pyrazolyl | B-5 | n/a |
| 36 | H | —NHCONHPh | B-1 | n/a |
| 37 | H | —NHCONHPh—4-CN | B-8 | n/a |
| 38 | H | —NHCONHBu—t | B-8 | n/a |
| 39 | H | —NHCOOEt | B-8 | n/a |

TABLE I-continued
| | | | | |
|---|---|---|---|---|
| 40 | H | —NHCOOCH₂Ph | B-7 | n/a |
| 41 | H | —NHCOOPh—2,4-(Bu—t)₂ | B-9 | n/a |
| 42 | H | —NHCO—2-Furyl | B-7 | n/a |
| 43 | H | —NHCOC₄H₉—t | B-9 | 126–129 |
| 47 | H | —NHCOC₄H₉—t | B-10 | 145–149 |
*Comparative compounds
Me herein means methyl. Et herein means ethyl.
Bu herein means butyl. Ph herein means phenyl.
Structural Representations for V in Table I are
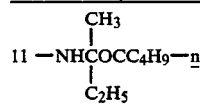
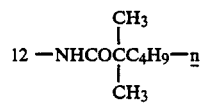
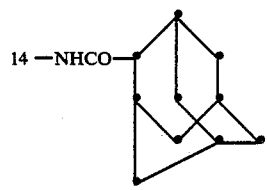
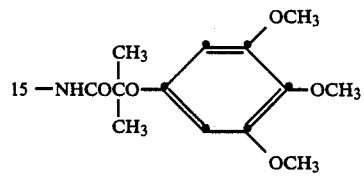
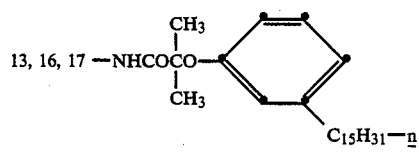
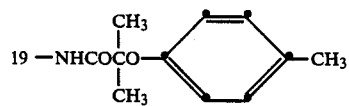
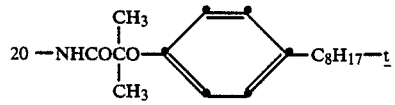
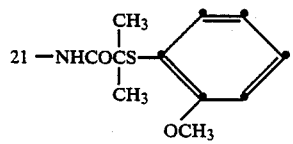

TABLE I-continued
26 —NHCO— 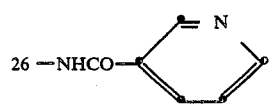
27 —NHCO— 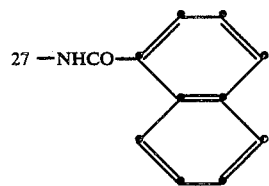
28 —NHCO— 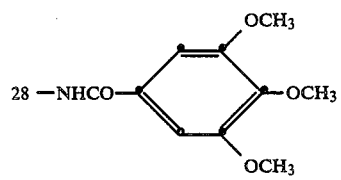
32 —NHCO— 
30, 33 —NHCO— 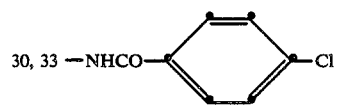
29, 34 —NHCO— 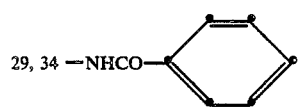
31 —NHCO— 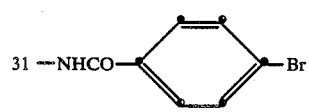
35 —NHCOC— 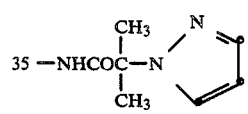
36 —NHCONH— 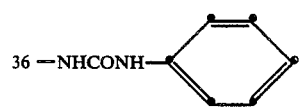
37 —NHCONH— 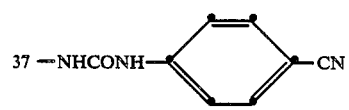
38 —NHCONHC₄H₉—t
39 —NHCOOC₂H₅
40 —NHCOOCH₂— 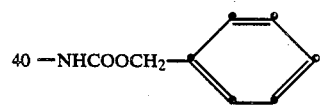

TABLE I-continued

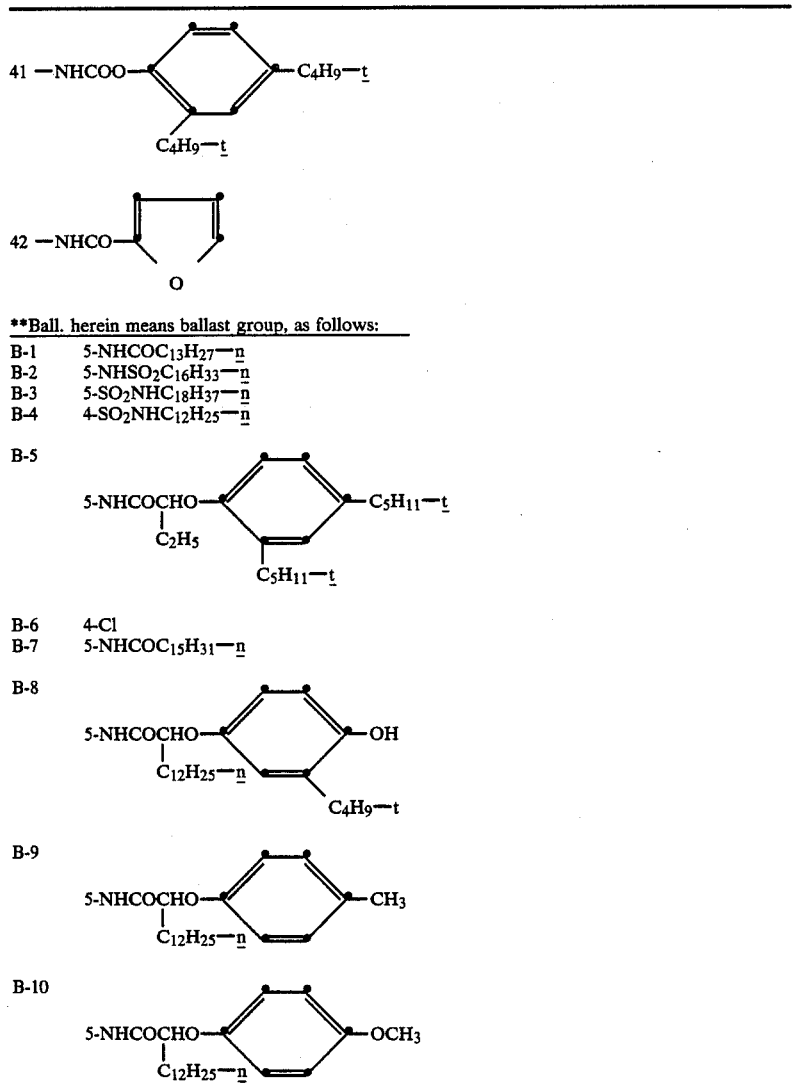

**Ball. herein means ballast group, as follows:

- B-1  5-NHCOC$_{13}$H$_{27}$—$\underline{n}$
- B-2  5-NHSO$_2$C$_{16}$H$_{33}$—$\underline{n}$
- B-3  5-SO$_2$NHC$_{18}$H$_{37}$—$\underline{n}$
- B-4  4-SO$_2$NHC$_{12}$H$_{25}$—$\underline{n}$ B-6  4-Cl
B-7  5-NHCOC$_{15}$H$_{31}$—$\underline{n}$ The couplers of this invention can be used in the ways and for the purposes that couplers are used in the photographic art.

Typically, the couplers are incorporated in silver halide emulsions and the emulsions coated on a support to form a photographic element. Alternatively, the coupler can be incorporated in photographic elements adjacent to the silver halide emulsion where, during development, the coupler will be in reactive association with development products such as oxidized color developing agent. Thus, as used herein, the term "associated therewith" signifies that the coupler is in the silver halide emulsion layer or in an adjacent location where, during processing, the coupler is capable of reacting with silver halide development products.

The photographic elements can be single color elements or multicolor elements. Multicolor elements contain dye image-forming units sensitive to each of the three primary regions of the spectrum. Each unit can be comprised of a single emulsion layer or of multiple emulsion layers sensitive to a given region of the spectrum. The layers iof the element, including the layers of the image-forming units, can be arranged in various orders as known in the art. In an alternative format, the emulsions sensitive to each of the three primary regions of the spectrum can be disposed as a single segmented layer, e.g., as by the use of microvessels as described in U.S. Pat. No. 4,362,806.

A typical multicolor photographic element comprises a support bearing a cyan dye image-forming unit comprised of at least one red-sensitive silver halide emulsion layer having associated therewith at least one cyan dye-forming coupler, a magenta dye image-forming unit comprising at least one green-sensitive silver halide emulsion layer having associated therewith at least one magenta dye-forming coupler and a yellow dye image-forming unit comprising at least one blue-sensitive silver halide emulsion layer having associated therewith at least one yellow dye-forming coupler, at least one of the couplers in the element being a coupler of this invention. The element can contain additional layers, such as filter layers, interlayers, overcoat layers, subbing layers, and the like.

In the following discussion of materials for use in the emulsions and elements of this invention, reference will be made to *Research Disclosure,* December, 1978, Item 14643, published by Industrial Opportunities Ltd., Homewell Havant, Hampshire, P09 1EF, U.K., the disclosures of which are incorporated herein by reference. This publication will be identified hereafter by the term "Research Disclosure".

The silver halide emulsions employed in the elements of this invention can be either negative-working or positive-working. Examples of emulsions and their preparation are described in Research Disclosure Sections I and II and the publications cited therein. Tabular photographic silver halide grains are also useful. Such tabular grain silver halide is described in, for example, U.S. Pat. No. 4,434,226 and Research Disclosure, January 1983, Item No. 22534. Examples of useful vehicles for the emulsion layers and other layers of elements of this invention are described in Research Disclosure Section IX and the publications cited therein.

In addition to the couplers of this invention, the elements of the invention can include additional couplers as described in Research Disclosure Section VII, paragraphs D, E, F and G and the publications cited therein. These couplers can be incorporated in the elements and emulsions as described in Research Disclosure Section VII, paragraph C and the publications cited therein.

The photographic elements of this invention or individual layers thereof, can contain brighteners (see Research Disclosure Section V), antifoggants and stabilizers (see Research Disclosure Section VI), antistain agents and image dye stabilizer (see Research Disclosure Section VII, paragraphs I and J), light absorbing and scattering materials (see Research Disclosure Section VIII), matting agents (see Research Disclosure Section XVI) and development modifiers (see Research Disclosure Section XXI).

The photographic elements can be coated on a variety of supports as described in Research Disclosure Section XVII and the references described therein.

Photographic elements can be exposed to actinic radiation, typically in the visible region of the spectrum, to form a latent image as described in Research Disclosure Section XVIII and then processed to form a visible dye image as described in Research Disclosure Section XIX. Processing to form a visible dye image includes the step of contacting the element with a color developing agent to reduce developable silver halide and oxidize the color developing agent. Oxidized color developing agent in turn reacts with the coupler to yield a dye.

Preferred color developing agents are p-phenylene diamines. Especially preferred are 4-amino-3-methyl-N,N-diethylaniline hydrochloride,
4-amino-3-methyl-N,N-diethylaniline hydrochloride,
4-amino-3-methyl-N-ethyl-N-β-(methanesulfonamido)ethylaniline sulfate hydrate,
4-amino-3-methyl-N-ethyl-N-β-hydroxyethylaniline sulfate,
4-amino-3-β-(methanesulfonamido)ethyl-N,N-diethylaniline hydrochloride and
4-amino-N-ethyl-N-(2-methoxyethyl)-m-toluidine di-p-toluene sulfonic acid.

With negative working silver halide a negative image can be formed. Optionally positive (or reversal) image can be formed.

Development is followed by the conventional steps of bleaching, fixing, or bleach-fixing, to remove silver and silver halide, washing and drying.

The following examples are included for a further understanding of this invention.

EXAMPLES 1–3

Photographic elements were prepared by coating a gel-subbed, polyethylene-coated paper support with a photosensitive layer containing a silver bromoiodide emulsion at 0.215 g Ag/m² (or 0.334 g for 4-equivalent couplers) gelatin at 1.62 g/m², and the magenta image coupler indicated in Table I at 0.38 mmol/m² dispersed in an equal weight of tricresyl phosphate. Each coupler dispersion also contained the following addenda (weight percent of coupler): A-1 (49%), A-2 (29%), A-3 (32%), A-4 (16%) and ethyl acetate (300%). The photosensitive layer was overcoated with a protective layer containing gelatin at 1.08 g/m² and bisvinylsulfonylmethyl ether hardener at 2 weight percent based on total gelatin.

Addendum A-1: (Compound No. I-1 in U.S. 4,217,410)

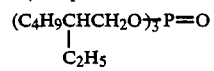

Addendum A-2: (Compound No. 21 in U.S. 4,360,589)

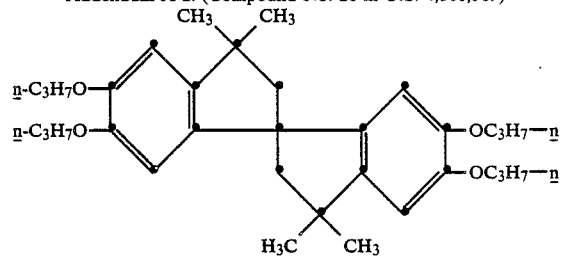

Addendum A-3: (Compound No. II-10 in EP 81,768)

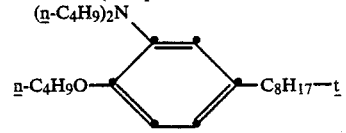

Addendum A-4: (Compound No. 104 in EP 69,070)

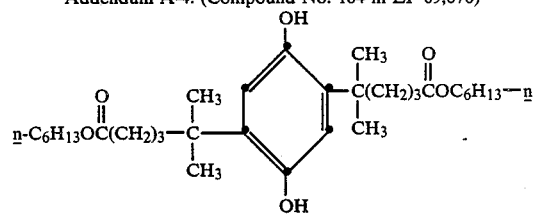

Samples of each element were imagewise exposed through a graduated-density test object, processed at 33° C. for 3.25 minutes in the color developer, 1.5 minutes in the bleach-fix bath, washed and dried. The components of the processing compositions were as follows:

| Color Developer (pH 10.08) | | |
|---|---|---|
| Triethanolamine | 11 | mL |
| Benzyl alcohol | 14.02 | mL |
| Lithium chloride | 2.0 | g |
| Potassium bromide | 0.6 | g |
| Hydroxylamine sulfate | 3.2 | g |
| Potassium sulfite (45% solution) | 2.8 | mL |
| 1-Hydroxyethylene-1,1-di-phosphoric acid (60%) | 0.8 | mL |
| 4-Amino-3-methyl-N—ethyl-N—(β-methanesulfonamido)ethylaniline sulfate hydrate | 4.35 | g |

-continued

| | | |
|---|---|---|
| Potassium carbonate (anhydrous) | 28 | g |
| Stilbene whitening agent | 0.6 | g |
| Surfactant | 1 | mL |
| Water to make | 1.0 | L |
| Bleach-Fix Bath (pH 6.8) | | |
| Ammonium thiosulfate | 104 | g |
| Sodium hydrogen sulfite | 13 | g |
| Ferric ammonium ethylenediamine tetraacetic acid (EDTA) | 65.5 | g |
| EDTA | 6.56 | g |
| Ammonium hydroxide (28%) | 27.9 | mL |
| Water to make | 1 | L |

Dye images of replicate processed strips were then subjected to 4-week fading under a 50 Klux xenon exposure, using a Wratten 2B filter to remove the ultraviolet component.

The results are presented as Examples 1, 2 and 3 in the following Table II.

It can be seen from the data that images formed from couplers of the invention show less light fading than those produced from closely related comparison couplers which have a primary alkylamido substituted phenylthio coupling-off group.

EXAMPLES 4-9

(Rapid Color Processing)

Photographic elements were prepared by coating a gel-subbed, polyethylene-coated paper support with a photosensitive layer containing a silver chloride emulsion at 0.172 g Ag/m$^2$ (or 0.2865 for 4-equivalent couplers), gelatin at 1.238 g/m$^2$, and a magenta image coupler indicated below at 0.38 mmol/m$^2$ dispersed in an equal weight of tricresyl phosphate. Each coupler dispersion also contained the following addenda (weight percent of coupler): A-1 (48%), A-2 (29%), A-3 (32%), A-4 (16%), and ethyl acetate layer containing gelatin at 1.08 g/m$^2$ and bisvinylsulfonylmethyl ether hardener at 2 weight percent based on total gelatin.

Samples of each element were imagewise exposed through a graduated density test object, then processed at 35° C. (45 seconds in a color developer, 45 seconds in the bleach-fix bath of Examples 1-3) washed and dried. The color developer used is disclosed in U.S. patent application No. 822,097 of Vincent et al filed Jan. 24, 1986.

The processed strips were subjected to a 2-week or 4-week xenon exposure as described in Examples 1-3. The results presented in Table II for Examples 4 through 9 show that the couplers of the invention generally give dyes of improved light stability over the dyes formed from the comparison couplers.

Under this rapid-access processing condition, the sample containing comparison Coupler A gave a maximum dye density of only 1.25, while that containing inventive Coupler 2 gave 2.52. The comparison sample evidently formed a significant proportion of leuco dye, since further bleaching in ferricyanide brought the maximum density up to 2.58. The sample of the invention also gave a more desirable bathochromically shifted spectral absorption (537 nm) than comparison Coupler A (536 nm).

TABLE II

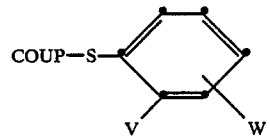

| Exp 1. | Cmpd. | W | V | Ball. | 4-Wk. |
|---|---|---|---|---|---|
| 1a | 2 | H | —NHCOBu—t | B-1 | −0.51 |
| 1b | 27 | H | —NHCOPr—i | B-1 | −0.56 |
| 1c | A* | 5-C$_8$H$_{17}$—t | —OBu—$\underline{n}$ | B-1 | −0.61 |
| 1d | C* | H | —NHCOC$_{11}$H$_{23}$—$\underline{n}$ | B-1 | −0.79 |
| 1e | D* | H | —NHCOC$_7$H$_{15}$—$\underline{n}$ | B-1 | −0.85 |
| 2a | 6 | H | —NHCOBu—t | B-3 | −0.28 |
| 2b | 24 | H | —NHCOCH(Et)Bu | B-3 | −0.34 |
| 2c | 25 | H | —NHCOCH(Et)Bu | B-2 | −0.42 |
| 2d | 26 | H | —NHCOCH(Et)Bu | B-4 | −0.49 |
| 2e | A* | 5-C$_8$H$_{17}$—t | —OBu—$\underline{n}$ | B-1 | −0.50 |
| 2f | E* | H | —NHCOC$_{11}$H$_{23}$—$\underline{n}$ | B-2 | −0.59 |
| 2g | F* | H | —NHCOC$_{11}$H$_{23}$—$\underline{n}$ | B-4 | −0.60 |
| 2h | G* | H | —NHCOC$_{11}$H$_{23}$—$\underline{n}$ | B-3 | −0.79 |
| 3a | 4 | H | —NHCOBu—t | B-2 | −0.33 |
| 3b | 5 | H | —NHCOBu—t | B-4 | −0.37 |
| 3c | A* | 5-C$_8$H$_{17}$—t | —OBu—$\underline{n}$ | B-1 | −0.41 |
| 3d | B* | (Coupling-off group is hydrogen) | | B-8 | −0.42 |
| 4a | 1 | H | —NHCOBu—t | B-5 | −0.27 |
| 4b | 2 | H | —NHCOBu—t | B-1 | −0.30 |
| 4c | 7 | 4-NHCOBu—t | —NHCOBu—t | B-2 | −0.30 |
| 4d | 8 | 4-NHCOBu—t | —NHCOBu—t | B-4 | −0.33 |
| 4e | 9 | 4-NHCOBu—t | —NHCOBu—t | B-5 | −0.34 |
| 4f | 10 | 4-NHCOBu—t | —NHCOBu—t | B-1 | −0.38 |
| 4g | A* | 5-C$_8$H$_{17}$—t | —OBu—$\underline{n}$ | B-1 | −0.41 |
| 5a | 16 | H | —NHCOC(Me,Me)OPh—3-C$_{15}$H$_{31}$—$\underline{n}$ | B-5 | −0.21 |
| 5b | 18 | H | —NHCOC(Me,Me)OPh—4-OC$_8$H$_{17}$—$\underline{n}$ | B-5 | −0.25 |
| 5c | 19 | H | —NHCOC(Me,Me)OPh—4-Me | B-5 | −0.28 |
| 5d | 2 | H | —NHCOBu—t | B-1 | −0.29 |
| 5e | A* | 5-C$_8$H$_{17}$—t | —OBu—$\underline{n}$ | B-1 | −0.27 |
| 6a | 23 | H | —NHCOC(Me,Me)SPh—2-OMe | B-5 | −0.35 |
| 6b | 2 | H | —NHCOBu—t | B-1 | −0.39 |
| 6c | 30 | H | —NHCOPh—3,4,5-(OMe)$_3$ | B-5 | −0.40 |
| 6d | 20 | H | —NHCOC(Me,Me)OPh—4-C$_8$H$_{17}$—t | B-5 | −0.43 |

TABLE II-continued

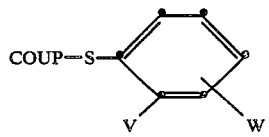

| Exp 1. | Cmpd. | W | V | Ball. | |
|---|---|---|---|---|---|
| 6e | B* | | (Coupling-off group is hydrogen) | B-8 | −0.51 |
| 7a | 46 | H | —NHCOBu—t | B-10 | −0.22 |
| 7b | 47 | H | —NHCOBu—t | B-9 | −0.25 |
| 7c | 2 | H | —NHCOBu—t | B-1 | −0.34 |
| 7d | B* | | (Coupling-off group is hydrogen) | B-8 | −0.40 |
| | | | | | 2-Wk. |
| 8a | 42 | H | —NHCOOEt | B-8 | −0.13 |
| 8b | 3 | H | —NHCOBu—t | B-8 | −0.13 |
| 8c | 32 | H | —NHCOPh | B-8 | −0.15 |
| 8d | 33 | H | —NHCOPh—4-Cl | B-8 | −0.16 |
| 8e | 34 | H | —NHCOPh—4-Br | B-8 | −0.17 |
| 8f | 41 | H | —NHCONHBu—t | B-8 | −0.17 |
| 8g | 29 | H | —NHCO—1-Naphthyl | B-8 | −0.19 |
| 8h | 40 | H | —NHCONHPh—4-CN | B-8 | −0.21 |
| 8I | B* | | (Coupling-off group is hydrogen) | B-8 | −0.18 |
| 9a | 17 | H | —NHCOC(Me,Me)OPh—3-$C_{15}H_{31}$—n | B-6 | −0.17 |
| 9b | 20 | H | —NHCOC(Me,Me)OPh—4-$C_8H_{17}$—t | B-5 | −0.17 |
| 9e | 23 | H | —NHCOC(Me,Me)SPh—2-OMe | B-5 | −0.19 |
| 9f | 13 | H | —NHCOC(Me,Me)OPh—3-$C_{15}H_{31}$—n | B-1 | −0.19 |
| 9g | 2 | H | —NHCOBu—t | B-1 | −0.20 |
| 9h | H* | | (Coupling-off group is hydrogen) | B-4 | −0.25 |

Other examples of couplers that provide useful results are ballasted couplers, such as:

EXAMPLE 10

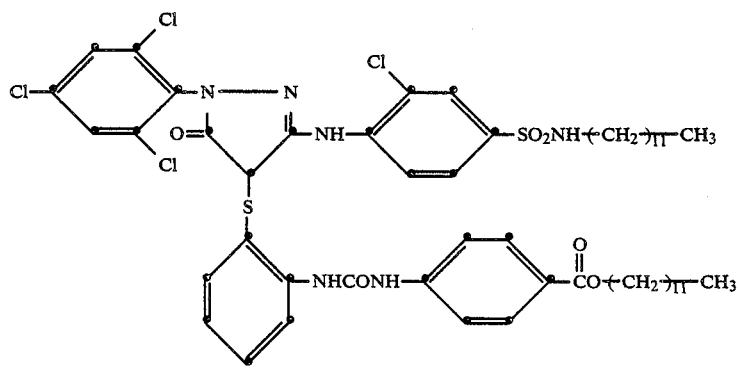

EXAMPLE 11

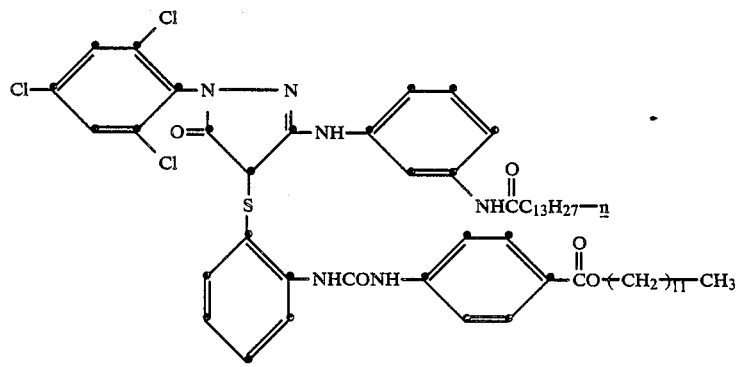

The invention has been described in detail with particular reference to preferred embodiments thereof, but it will be understood that variations and modifications can be effected with the spirit and scope of the invention.

What is claimed is:

1. A photographic element comprising a support and at least one silver halide emulsion layer having associated therewith a pyrazolone photographic coupler having in the coupling position a coupling-off group represented by the formula:

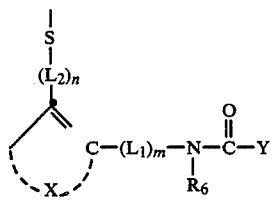

wherein:
L$_1$ and L$_2$ individually are unsubstituted or substituted methylene or ethylene;
m and n individually are 0 or 1;
Y is R$_1$ or ZR$_2$;
R$_1$ is an unsubstituted or substituted aryl or heterocyclic group, or a secondary or tertiary carbon group represented by

wherein
R$_3$ and R$_4$ individually are selected from the group consisting of halogen, R$_2$ and Z$_1$R$_b$, or join together, with or without R$_5$, to form one or two unsubstituted or substituted alicyclic or heterocyclic rings;
Z is O, S, or NR$_a$;
Z$_1$ is O, S, or NR$_c$;
R$_2$ is an unsubstituted or substituted alkyl, aryl or heterocyclic group;
R$_5$ is hydrogen, halogen, an unsubstituted or substituted alkyl, aryl, or heterocyclic group or Z$_1$R$_b$, or joins together with at least one of R$_3$ and R$_4$ to form one or two unsubstituted or substituted alicyclic or heterocyclic rings;
R$_6$, R$_a$ and R$_c$ are individually alkyl, aryl or heterocyclic groups;
R$_b$ is an unsubstituted or substituted alkyl, aryl or heterocyclic group when Z$_1$ is O then R$_b$ is othe than substituted phenyl; and
X represents atoms selected from the group consisting of carbon, oxygen, nitrogen, and sulfur atoms necessary to complete a 5-, 6-, or 7-member unsubstituted or substituted unsaturated ring.

2. A photographic element as in claim 1 wherein the pyrazolone coupler is a magenta dye image-forming coupler.

3. A photographic element as in claim 1 wherein Y is tertiary-butyl, tertiary-pentyl or tertiary-hexyl.

4. A photographic element as in claim 1 wherein the pyrazolone coupler is represented by the formula:

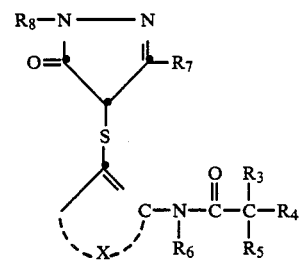

wherein:
R$_3$ and R$_4$ individually are selected from the group consisting of halogen, R$_2$, and Z$_1$R$_b$;
Z$_1$ is O, S or NR$_c$;
R$_2$ is an unsubstituted or substituted alkyl, aryl, or heterocyclic group;
R$_5$ is hydrogen, halogen, R$_2$ or Z$_1$R$_b$;
R$_6$ is hydrogen or an unsubstituted or substituted alkyl, aryl or heterocyclic group;
R$_7$ is an anilino, acylamino, ureido, carbamoyl, alkoxy, aryloxycarbonyl, alkoxycarbonyl, or N-heterocyclic group;
R$_8$ is unsubstituted or substituted aryl; and,
R$_b$ is an unsubstituted or substituted alkyl, aryl or heterocyclic group, and when Z$_1$ is O then R$_b$ is other than substituted phenyl;
R$_c$ is an unsubstituted or substituted alkyl, aryl or heterocyclic group; and
X represents atoms selected from the group consisting of carbon, oxygen, nitrogen, and sulfur atoms necessary to complete a 5-, 6-, or 7-member unsubstituted or substituted ring.

5. A photographic element as in claim 1 wherein the pyrazolone coupler is represented by the formula:

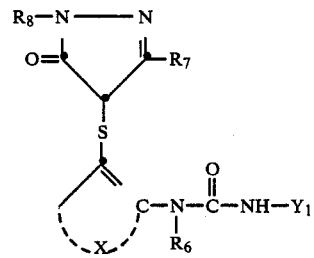

wherein:
Y$_1$ is an unsubstituted or substituted alkyl, aryl or heterocyclic group;
R$_6$ is hydrogen or an unsubstituted or substituted alkyl, aryl or heterocyclic group;
R$_7$ is an anilino, acylamino, ureido, carbamoyl, alkoxy, aryloxycarbonyl, alkoxycarbonyl or N-heterocyclic group;
R$_8$ is unsubstituted or substituted aryl;
X represents atoms selected from the group consisting of carbon, oxygen, nitrogen, and sulfur atoms necessary to complete a 5-, 6-, or 7-member unsubstituted or substituted ring.

6. A photographic element as in claim 1 wherein the coupling-off group is

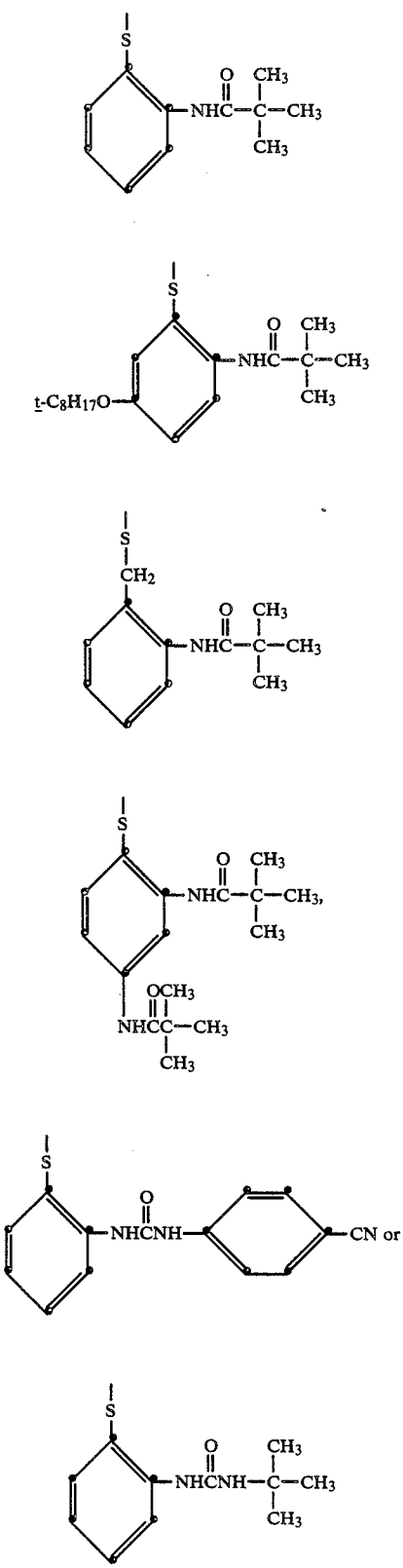
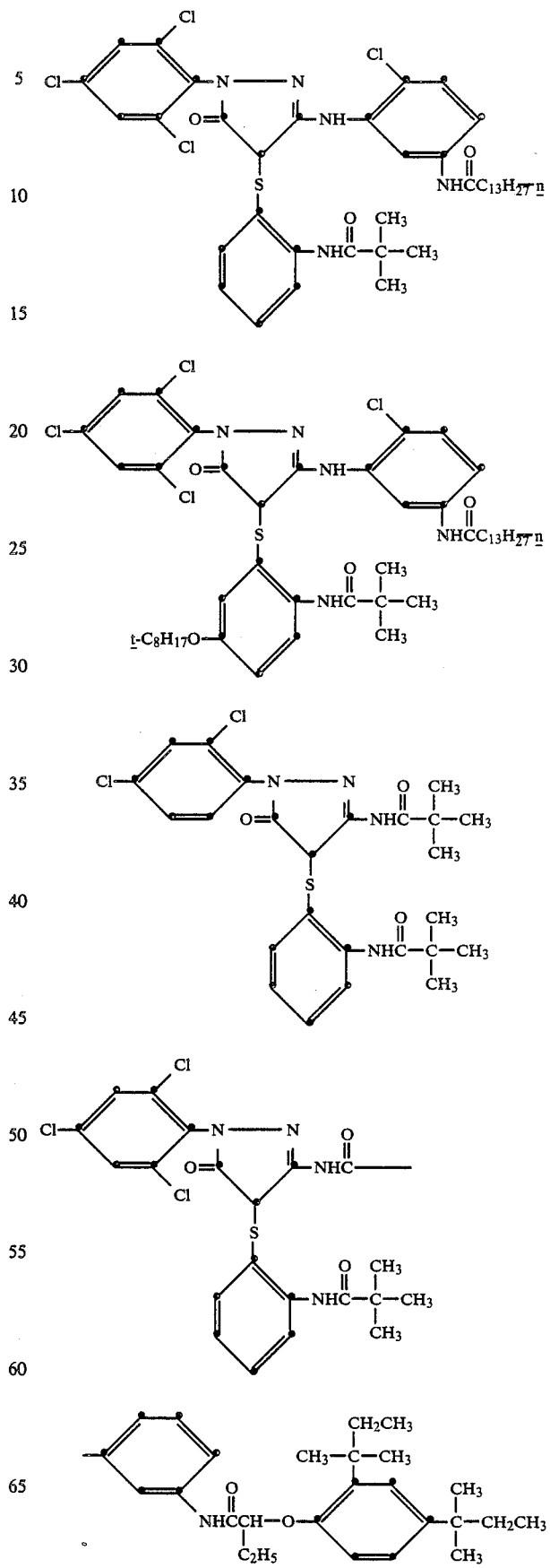
7. A photographic element as in claim 1 wherein the pyrazolone coupler is

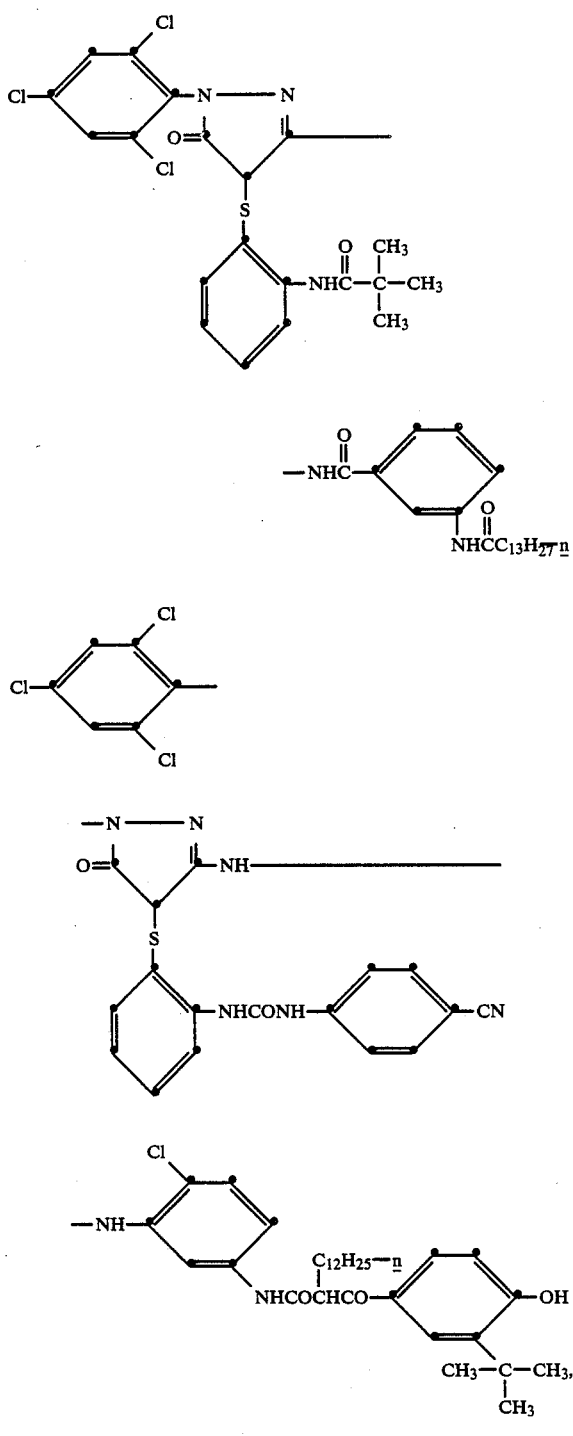

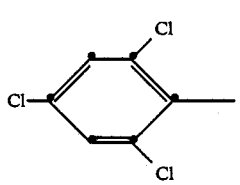

or

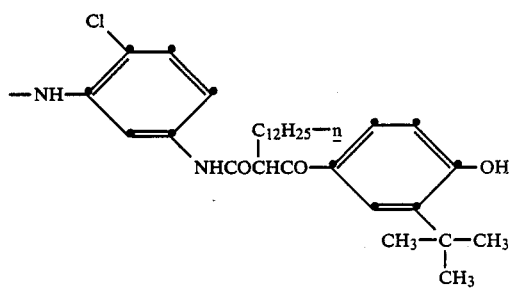

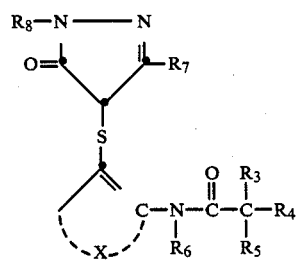

8. A photographic element as in claim 1 comprising a support bearing a red-sensitive silver halide emulsion unit having associated therewith a cyan-dye image-forming material, a green-sensitive silver halide emulsion unit having associated therewith a magenta dye image-forming material, and a blue-sensitive silver halide emulsion unit having associated therewith a yellow dye image-providing material, wherein at least one of the silver halide emulsion units has said pyrazolone coupler associated therewith.

9. A process of forming a photographic image which comprises developing an exposed silver halide photographic emulsion layer with a color developing agent in the presence of a pyrazolone photographic coupler as defined in claim 1.

10. A process as in claim wherein the pyrazolone photographic coupler is represented by the formula:

wherein:
$R_3$ and $R_4$ individually are selected from the group consisting of halogen, $R_2$, and $Z_1R_b$;
$Z_1$ is O, S or $NR_c$;
$R_2$ is an unsubstituted or substituted alkyl, aryl, or heterocyclic group;
$R_5$ is hydrogen, halogen, $R_2$ or $Z_1R_b$;
$R_6$ is hydrogen or an unsubstituted or substituted alkyl, aryl or heterocyclic group;
$R_7$ is an anilino, acylamino, ureido, carbamoyl, alkoxy, aryloxycarbonyl, alkoxycarbonyl, or N-heterocyclic group;
$R_8$ is unsubstituted or substituted aryl; and, $R_b$ is an unsubstituted or substituted alkyl, aryl or heterocyclic group and when $Z_1$ is O then $R_b$ is other than substituted phenyl;

$R_c$ is an unsubstituted or substituted alkyl, aryl or heterocyclic group; and

X represents atoms selected from the group consisting of carbon, oxygen, nitrogen, and sulfur atoms necessary to complete a 5-, 6-, or 7-member unsubstituted or substituted unsaturated ring.

11. A process as in claim 9 wherein the pyrazolone coupler is:

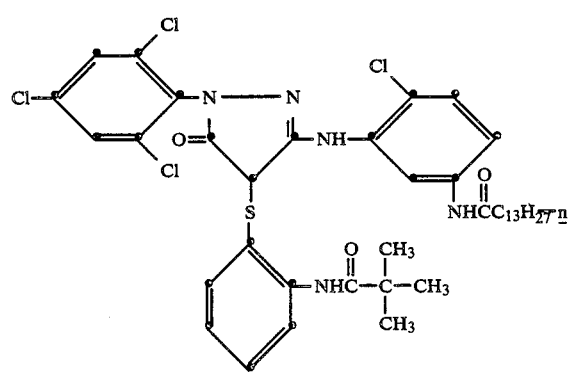

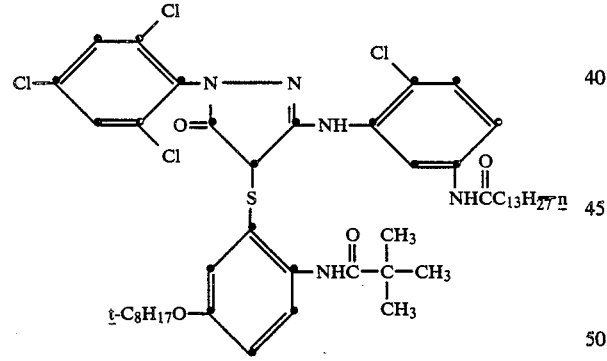

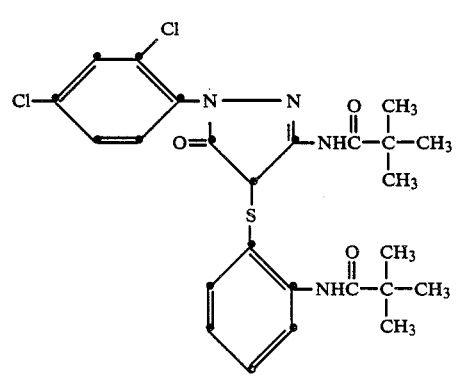

-continued

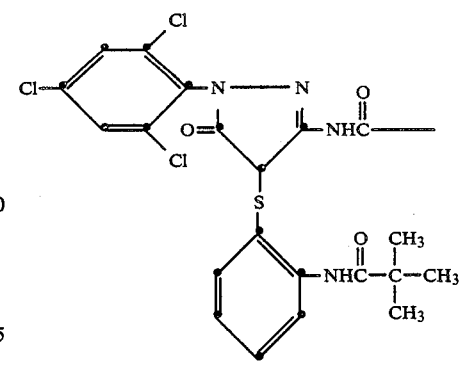

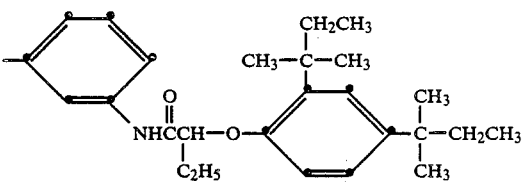

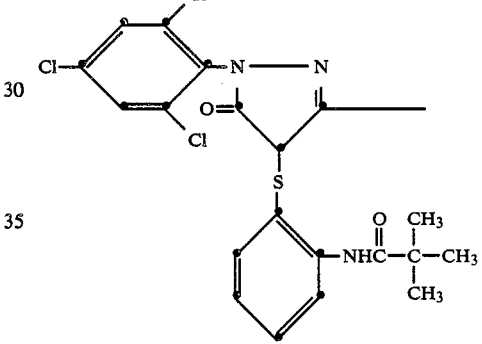

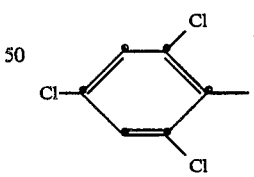

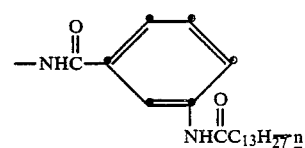

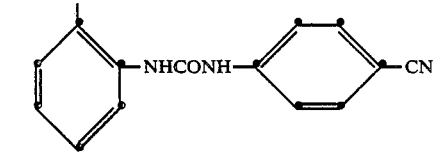

-continued

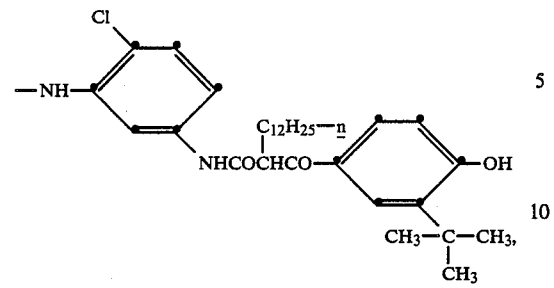

or

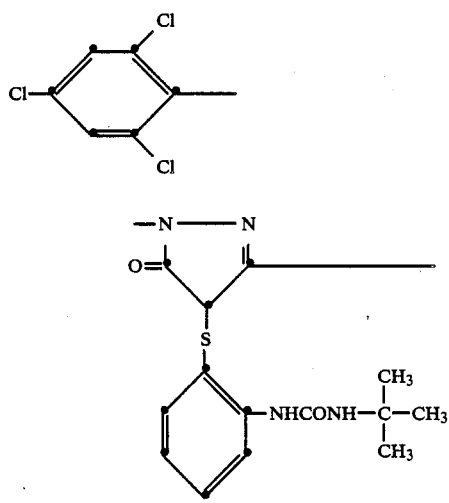

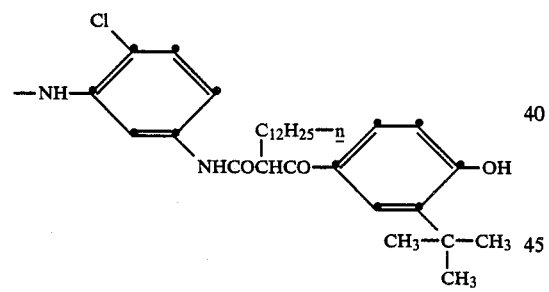

12. A photographic element comprising a support bearing a red-sensitive silver halide emulsion layer unit having associated therewith a cyan dye image-forming coupler, a green-sensitive silver halide emulsion layer unit having associated therewith a magneta dye image-forming coupler and a blue-sensitive silver halide emulsion layer unit having associated therewith a yellow dye image-forming coupler, wherein the magneta dye image-forming coupler is represented by the formula:

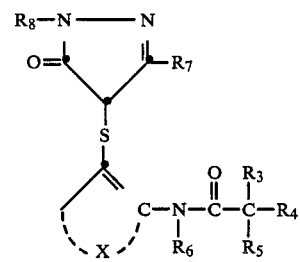

wherein:
R$_3$ and R$_4$ individually are selected from the group consisting of halogen, R$_2$, and Z$_1$R$_b$;
Z$_1$ is O, S or NR$_c$;
R$_2$ is an unsubstituted or substituted alkyl, aryl, or heterocyclic group;
R$_5$ is hydrogen, halogen, R$_2$ or Z$_1$R$_b$;
R$_6$ is hydrogen or an unsubstituted or substituted alkyl, aryl or heterocyclic group;
R$_7$ is an anilino, acylamino, ureido, carbamoyl, alkoxy, aryloxycarbonyl, alkoxycarbonyl, or N-heterocyclic group;
R$_8$ is unsubstituted or substituted aryl; and,
R$_8$ is an unsubstituted or substituted alkyl, aryl or heterocyclic group, and when Z$_1$ is O then R$_b$ is other than substituted phenyl;
R$_c$ is an unsubstituted or substituted alkyl, aryl or heterocyclic group; and
X represents atoms selected from the group consisting of carbon, oxygen, nitrogen, and sulfur atoms necessary to complete a 5-, 6-, or 7-member unsubstituted or substituted ring.

13. A photographic element as in claim 12 wherein the magenta image-forming coupler is:

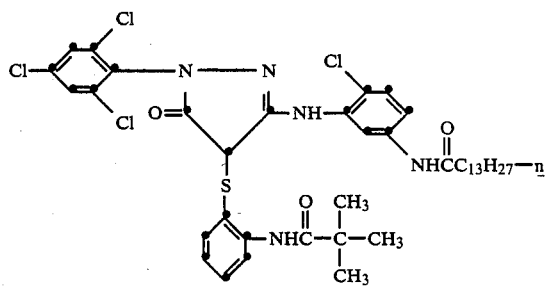

* * * * *

UNITED STATES PATENT AND TRADEMARK OFFICE
CERTIFICATE OF CORRECTION

PATENT NO. : 4,853,319
DATED : August 1, 1989
INVENTOR(S) : Krishnamurthy et al

It is certified that error appears in the above-identified patent and that said Letters Patent is hereby corrected as shown below:

Column 41, line 50, after "individually" insert -- hydrogen, unsubstituted or substituted -- ;

Column 41, line 54, "othe" should read -- other --;

Column 46, line 41, after "claim" insert -- 9 --;

Column 50, line 30, "$R_8$" should read -- $R_b$ --.

Signed and Sealed this

Sixteenth Day of April, 1991

Attest:

Attesting Officer

HARRY F. MANBECK, JR.

Commissioner of Patents and Trademarks